US009610093B2

(12) United States Patent
Sabir et al.

(10) Patent No.: US 9,610,093 B2
(45) Date of Patent: *Apr. 4, 2017

(54) MICROBLISTER SKIN GRAFTING

(71) Applicant: KCI Licensing, Inc., San Antonio, TX (US)

(72) Inventors: Sameer Ahmed Sabir, Cambridge, MA (US); Andrew Ziegler, Arlington, MA (US)

(73) Assignee: KCI Licensing, Inc., San Antonio, TX (US)

( * ) Notice: Subject to any disclaimer, the term of this patent is extended or adjusted under 35 U.S.C. 154(b) by 390 days.

This patent is subject to a terminal disclaimer.

(21) Appl. No.: 13/839,518

(22) Filed: Mar. 15, 2013

(65) Prior Publication Data
US 2013/0204273 A1    Aug. 8, 2013

Related U.S. Application Data

(63) Continuation-in-part of application No. 13/346,329, filed on Jan. 9, 2012, now Pat. No. 8,978,234, which is a continuation-in-part of application No. 13/346,318, filed on Jan. 9, 2012, now Pat. No. 9,173,674, which is a continuation-in-part of application No. 12/851,656, filed on Aug. 6, 2010, now Pat. No. 8,562,626, said application No.
(Continued)

(51) Int. Cl.
| A61B 17/50 | (2006.01) |
| A61B 17/322 | (2006.01) |
| A61B 17/00 | (2006.01) |
| A61B 18/08 | (2006.01) |
| A61B 18/14 | (2006.01) |

(52) U.S. Cl.
CPC .......... *A61B 17/322* (2013.01); *A61B 18/08* (2013.01); *A61B 2017/00761* (2013.01); *A61B 2017/3225* (2013.01); *A61B 2018/1412* (2013.01)

(58) Field of Classification Search
CPC ........ A61B 17/322; A61B 2017/00761; A61B 2017/3225; A61B 18/08; A61B 2018/1412
USPC ....................................... 606/132
See application file for complete search history.

(56) References Cited

U.S. PATENT DOCUMENTS 2,379,574 A    7/1945  Goldthwait
2,721,555 A    10/1955  Jenny
(Continued)

FOREIGN PATENT DOCUMENTS

CN    2596950 Y    1/2004
CN    101053528 A    10/2007
(Continued)

OTHER PUBLICATIONS

Awad, Chinese Cupping: A Simple Method to Obtain Epithelial Grafts for the Management of Resistant Localized Vitiligo, American Society of Dermatologic Surgery, Inc., Dermatol Surg, (2008), 34(9):1186-1193.
(Continued)

*Primary Examiner* — Robert Lynch
(74) *Attorney, Agent, or Firm* — Thomas Engellenner; Reza Mollaaghababa; Pepper Hamilton LLP

(57) ABSTRACT

The present invention generally relates to devices for harvesting a skin graft(s). The present invention provides a blister raising device integrated with a member for cutting the blister.

17 Claims, 24 Drawing Sheets

Related U.S. Application Data

13/839,518 is a continuation-in-part of application No. 12/851,621, filed on Aug. 6, 2010, now Pat. No. 8,617,181, and a continuation-in-part of application No. 12/851,703, filed on Aug. 6, 2010, now Pat. No. 8,926,631, and a continuation-in-part of application No. 12/851,682, filed on Aug. 6, 2010.

(60) Provisional application No. 61/567,946, filed on Dec. 7, 2011.

(56) References Cited

U.S. PATENT DOCUMENTS

| | | | |
|---|---|---|---|
| 3,054,404 A | | 9/1962 | Meek |
| 3,782,387 A * | | 1/1974 | Falabella ............... 128/898 |
| 4,345,374 A | | 8/1982 | Jacobson |
| 4,600,533 A | | 7/1986 | Chu |
| 4,605,010 A | | 8/1986 | McEwen et al. |
| 4,666,447 A | | 5/1987 | Smith |
| 4,679,324 A | | 7/1987 | Krik |
| 4,773,418 A | | 9/1988 | Hettich |
| 4,917,086 A | | 4/1990 | Feltovich et al. |
| 5,015,584 A | | 5/1991 | Brysk |
| 5,163,955 A * | | 11/1992 | Love et al. ............ 623/2.15 |
| 5,386,633 A | | 2/1995 | Kanno |
| 5,433,221 A * | | 7/1995 | Adair ..................... 128/849 |
| 5,441,490 A | | 8/1995 | Svedman |
| 5,460,939 A | | 10/1995 | Hansbrough |
| 5,476,478 A | | 12/1995 | Jackson |
| 5,489,304 A | | 2/1996 | Orgill |
| 5,496,339 A | | 3/1996 | Koepnick |
| 5,545,222 A | | 8/1996 | Bonutti |
| 5,571,098 A | | 11/1996 | Domankevitz |
| 5,595,570 A | | 1/1997 | Smith |
| 5,686,303 A | | 11/1997 | Korman |
| 5,730,717 A | | 3/1998 | Gelbfish |
| 5,759,193 A | | 6/1998 | Burbank |
| 5,817,115 A | | 10/1998 | Nigam |
| 5,888,219 A | | 3/1999 | Bonutti |
| 5,914,261 A | | 6/1999 | Boulton et al. |
| 5,914,264 A | | 6/1999 | Korman |
| 5,921,980 A | | 7/1999 | Kiru |
| 5,972,476 A | | 10/1999 | Field |
| 5,976,163 A | | 11/1999 | Nigam |
| 6,056,738 A | | 5/2000 | Marchitto |
| 6,063,094 A | | 5/2000 | Rosenberg |
| 6,071,247 A | | 6/2000 | Kennedy |
| 6,071,267 A | | 6/2000 | Zamierowski et al. |
| 6,080,166 A | | 6/2000 | McEwen et al. |
| 6,083,236 A | | 7/2000 | Feingold |
| 6,248,114 B1 | | 6/2001 | Ysebaert |
| 6,254,580 B1 | | 7/2001 | Svedman |
| 6,358,260 B1 | | 3/2002 | Ross |
| 6,364,908 B1 | | 4/2002 | Ysebaert |
| 6,402,770 B1 | | 6/2002 | Jessen |
| 6,436,078 B1 * | | 8/2002 | Svedman ................. 604/313 |
| 6,585,939 B1 | | 7/2003 | Dapprich |
| 6,612,310 B2 * | | 9/2003 | Sklar ..................... 128/849 |
| 6,623,498 B1 | | 9/2003 | Ziemer |
| 6,800,282 B1 | | 10/2004 | Thomson |
| 6,860,904 B2 | | 3/2005 | Bonutti |
| 7,056,327 B2 | | 6/2006 | Levesque et al. |
| 7,078,582 B2 | | 7/2006 | Stebbings |
| 7,137,979 B2 | | 11/2006 | Conrad et al. |
| 7,207,998 B2 | | 4/2007 | Feingold |
| 7,208,006 B2 | | 4/2007 | Fleischman |
| 7,244,444 B2 | | 7/2007 | Bates |
| 7,513,902 B2 | | 4/2009 | Banbury et al. |
| 7,540,875 B2 | | 6/2009 | Jessen |
| 7,625,384 B2 | | 12/2009 | Eriksson |
| 7,651,507 B2 | | 1/2010 | Mishra |
| 7,666,134 B2 | | 2/2010 | Eriksson |
| 7,666,192 B2 | | 2/2010 | Seegert |
| 7,708,746 B2 | | 5/2010 | Eriksson |
| 7,926,401 B2 | | 4/2011 | Mishra |
| 8,002,779 B2 | | 8/2011 | Barker et al. |
| 8,109,187 B2 | | 2/2012 | Mishra |
| 8,162,957 B2 | | 4/2012 | Mishra |
| 8,187,285 B2 | | 5/2012 | Eriksson |
| 8,562,626 B2 | | 10/2013 | Sabir |
| 8,617,181 B2 | | 12/2013 | Sabir |
| 8,926,631 B2 | | 1/2015 | Sabir |
| 9,173,674 B2 | | 11/2015 | Sabir et al. |
| 2001/0029380 A1 | | 10/2001 | Ysebaert |
| 2002/0052614 A1 | | 5/2002 | GeBauer |
| 2002/0092529 A1 | | 7/2002 | Rozier |
| 2003/0009185 A1 | | 1/2003 | Jessen |
| 2003/0212357 A1 | | 11/2003 | Pace |
| 2004/0097967 A1 | | 5/2004 | Ignon |
| 2004/0172045 A1 | | 9/2004 | Eriksson |
| 2004/0186498 A1 | | 9/2004 | Barnes et al. |
| 2004/0215217 A1 | | 10/2004 | Banbury |
| 2004/0225309 A1 | | 11/2004 | Eriksson |
| 2004/0230215 A1 | | 11/2004 | Eriksson |
| 2004/0237744 A1 | | 12/2004 | Lin |
| 2005/0038520 A1 | | 2/2005 | Binette |
| 2005/0076921 A1 | | 4/2005 | Rozier |
| 2005/0101972 A1 | | 5/2005 | Bhatavadekar |
| 2005/0221276 A1 | | 10/2005 | Rozakis et al. |
| 2005/0234485 A1 | | 10/2005 | Seegert |
| 2005/0244967 A1 | | 11/2005 | Pearlman |
| 2006/0079852 A1 | | 4/2006 | Bubb et al. |
| 2006/0141616 A1 | | 6/2006 | Guu |
| 2006/0173087 A1 | | 8/2006 | Hyde et al. |
| 2006/0271070 A1 | | 11/2006 | Eriksson |
| 2006/0287696 A1 * | | 12/2006 | Wright et al. ............... 607/88 |
| 2007/0183974 A1 | | 8/2007 | Pearlman |
| 2007/0255168 A1 | | 11/2007 | Hibner et al. |
| 2008/0146980 A1 | | 6/2008 | Rousso |
| 2009/0085286 A1 | | 4/2009 | Grist et al. |
| 2010/0012311 A1 | | 1/2010 | Colongo |
| 2010/0042127 A1 | | 2/2010 | Eriksson |
| 2010/0121311 A1 | | 5/2010 | Seegert et al. |
| 2010/0145360 A1 | | 6/2010 | Eriksson |
| 2010/0152651 A1 | | 6/2010 | Boyden et al. |
| 2010/0152750 A1 | | 6/2010 | Memar |
| 2010/0286635 A1 | | 11/2010 | Watson, Jr. |
| 2010/0310823 A1 | | 12/2010 | Albertelli et al. |
| 2011/0077664 A1 | | 3/2011 | Schulz |
| 2011/0251602 A1 | | 10/2011 | Anderson |
| 2011/0264115 A1 | | 10/2011 | Asrani |
| 2011/0282309 A1 | | 11/2011 | Adie et al. |
| 2012/0021186 A1 | | 1/2012 | Schneider |
| 2012/0035599 A1 | | 2/2012 | Sabir |
| 2012/0035618 A1 | | 2/2012 | Sabir |
| 2012/0035619 A1 | | 2/2012 | Sabir |
| 2012/0035620 A1 | | 2/2012 | Sabir |
| 2012/0041430 A1 | | 2/2012 | Anderson |
| 2012/0125798 A1 | | 5/2012 | Baecker et al. |
| 2012/0136323 A1 | | 5/2012 | Stasko et al. |
| 2012/0172894 A1 | | 7/2012 | Sabir |
| 2012/0197267 A1 | | 8/2012 | Sabir |
| 2012/0201755 A1 | | 8/2012 | Rozakis et al. |
| 2012/0201793 A1 | | 8/2012 | Bellomo |
| 2012/0244623 A1 | | 9/2012 | Patel |
| 2012/0271320 A1 | | 10/2012 | Hall |
| 2013/0041385 A1 | | 2/2013 | Giovannoli |
| 2013/0145596 A1 | | 6/2013 | Sabir et al. |
| 2013/0158627 A1 | | 6/2013 | Gozani |
| 2013/0204273 A1 | | 8/2013 | Sabir et al. |
| 2014/0277454 A1 | | 9/2014 | Locke et al. |
| 2015/0127077 A1 | | 5/2015 | Ben Asher et al. |
| 2015/0182241 A1 | | 7/2015 | Pratt |

FOREIGN PATENT DOCUMENTS

| | | |
|---|---|---|
| EP | 0099748 A1 | 2/1984 |
| EP | 1092515 A1 | 4/2001 |
| EP | 1614404 A2 | 1/2006 |
| EP | 2837370 A1 | 2/2015 |
| JP | 2009-095476 A | 5/2009 |
| SU | 772544 A1 | 10/1980 |
| WO | 9211879 A1 | 7/1992 |
| WO | 9528886 A1 | 11/1995 |

(56) References Cited

FOREIGN PATENT DOCUMENTS

| | | | |
|---|---|---|---|
| WO | 9618432 A1 | 6/1996 | |
| WO | 9633768 A2 | 10/1996 | |
| WO | 9720509 A2 | 6/1997 | |
| WO | 9816158 A1 | 4/1998 | |
| WO | 03020333 A2 | 3/2003 | |
| WO | 03039382 A2 | 5/2003 | |
| WO | 03049626 A1 | 6/2003 | |
| WO | 03049783 A2 | 6/2003 | |
| WO | 03068120 A1 | 8/2003 | |
| WO | 2004071313 A2 | 8/2004 | |
| WO | 2004075764 A1 | 9/2004 | |
| WO | 2004078032 A2 | 9/2004 | |
| WO | 2004105576 A2 | 12/2004 | |
| WO | 2005033273 A2 | 4/2005 | |
| WO | 2005046428 A2 | 5/2005 | |
| WO | 2007034438 A2 | 3/2007 | |
| WO | 2007117488 A2 | 10/2007 | |
| WO | 2010014716 A1 | 2/2010 | |
| WO | 2010036788 A2 | 4/2010 | |
| WO | WO2010/036788 * | 4/2010 | ........... A61B 17/322 |
| WO | 2011038326 A2 | 3/2011 | |
| WO | 2011059441 A1 | 5/2011 | |
| WO | 2011075676 A2 | 6/2011 | |
| WO | 2012019094 A2 | 2/2012 | |
| WO | 2012019095 A2 | 2/2012 | |
| WO | 2012019096 A1 | 2/2012 | |
| WO | 2012019098 A1 | 2/2012 | |
| WO | 2012102812 A1 | 8/2012 | |
| WO | 2012145504 A1 | 10/2012 | |
| WO | 20140152319 A2 | 9/2014 | |

OTHER PUBLICATIONS

Balaji et al., Isolation of a Novel Population of Multipotent Stem Cells From Epidermal Layer of Human Skin, Biology and Medicine, (2010), 2(2):57-67.
Kreis et al., Expansion techniques for skin grafts: comparison between mesh and Meek Island (sandwich-) grafts, Burns, (1994), 20(1):S39-S42.
Lari et al., Expansion technique for skins grafts (Meek technique) in the treatment of severely burned patients, Burns, (2001), 27:61-66.
Meek et al., Successful Microdermagrafting Using the Meek-Wall Microdermatome, Am J Surg, (1958), 96(4):557-558.
Mulekar et al., Treatment of Vitiligo on Difficult-to-Treat Sites Using Autologous Noncultured Cellular Grafting, Dermatol Surg., (2009), 25(1):66-71.
International Search Report and Written Opinion dated Dec. 16, 2011 for PCT/US11/46737.
International Search Report and Written Opinion dated Dec. 23, 2011 for PCT/US11/46739.
International Search Report and Written Opinion dated Dec. 16, 2011 for PCT/US11/46738.
International Search Report and Written Opinion dated Dec. 6, 2011 for PCT/US11/46741.
International Search Report and Written Opinion dated Feb. 15, 2013 for International Application No. PCT/US2012/068551, 9 pages.
International Search Report and Written Opinion dated Aug. 1, 2014 for International Application No. PCT/US2014/027237, 12 pages.
International Search Report and Written Opinion dated Oct. 2, 2014 for International Application No. PCT/US2014/027205, 19 pages.
International Search Report and Written Opinion dated Mar. 19, 2015 for PCT/US2014/072170, 12 pages.
International Search Report and Written Opinion dated Mar. 20, 2015 for PCT/US2014/072180, 10 pages.
International Search Report and Written Opinion dated Mar. 19, 2015 for PCT/US2014/072188, 12 pages.
Sams et al.. Useful adjuncts to harvest split-thickness skin grafts. Dermatol Surg. Dec. 2004;30(12 Pt 2):1591-2.
Weyandt et al., Split-skin grafting from the scalp: the hidden advantage. Dermatol Surg. Dec. 2009;35(12):1873-9.
[No Author Listed] BBC—GCSE Bitsize: Gore-Tex, Article: http://www.bbc.co.uk/schools/gcsebitesize/science/ocr_gateway_pre_2011/carbon_chem/6_designer_polymers3.shtml; retrieved Apr. 22, 2015.
Extended European Search Report mailed Mar. 3, 2016 received in European Application No. 14771124.6, 7 pages.
European Search Report mailed Apr. 17, 2015 received in European Application No. 12855127.2, 3 pages.

* cited by examiner

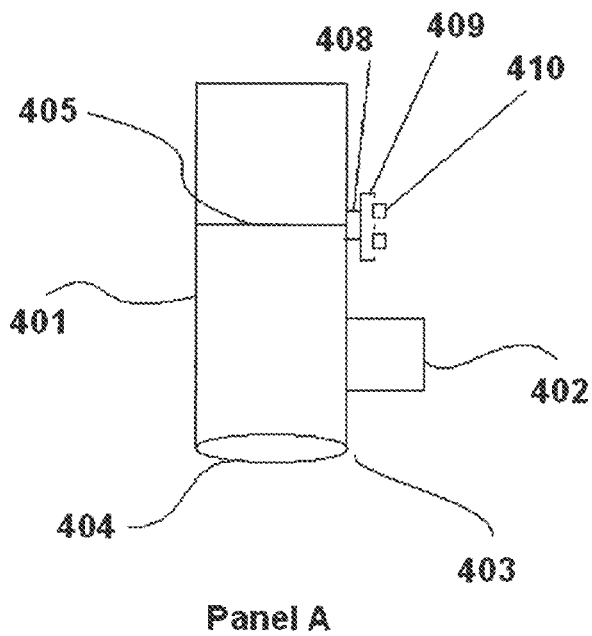
Panel A
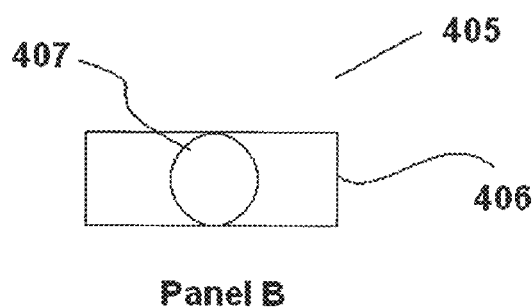
Panel B
Figure 3

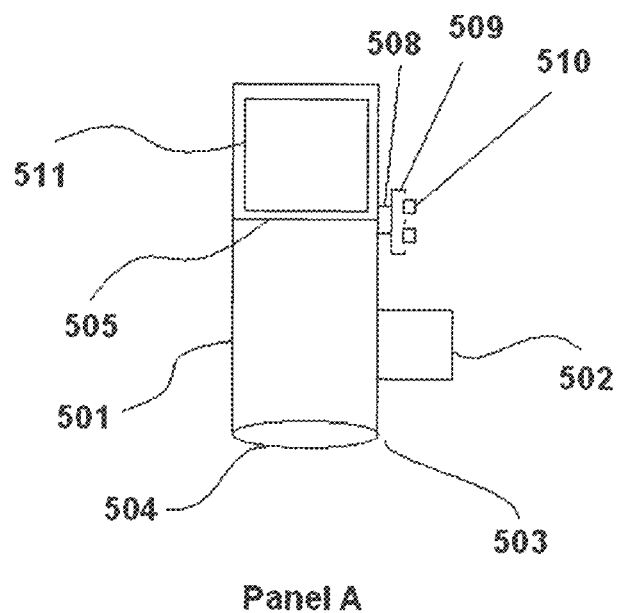
Panel A
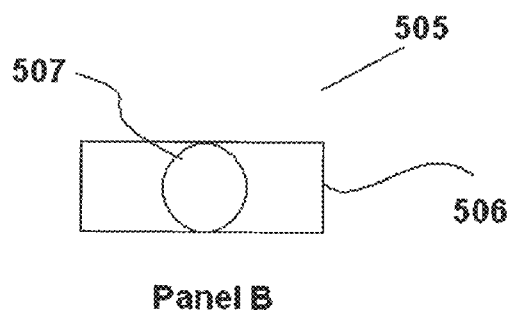
Panel B
Figure 4

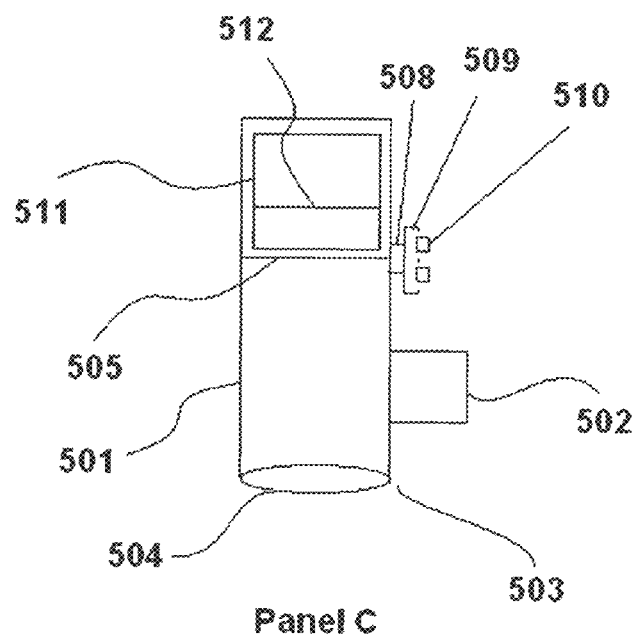
Panel C
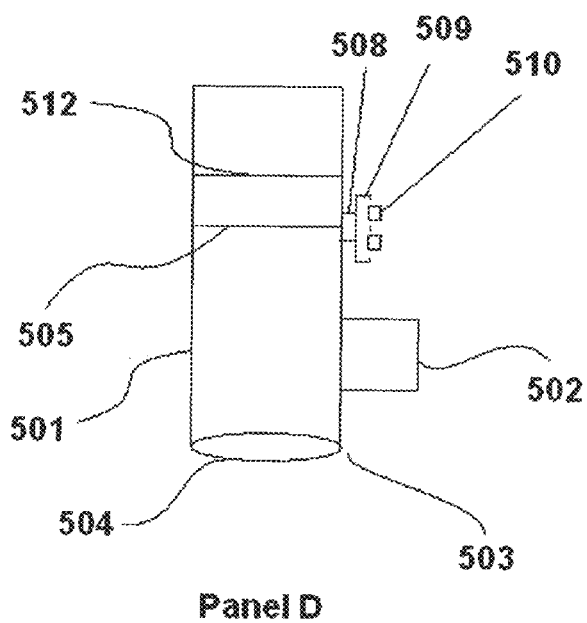
Panel D
Figure 4

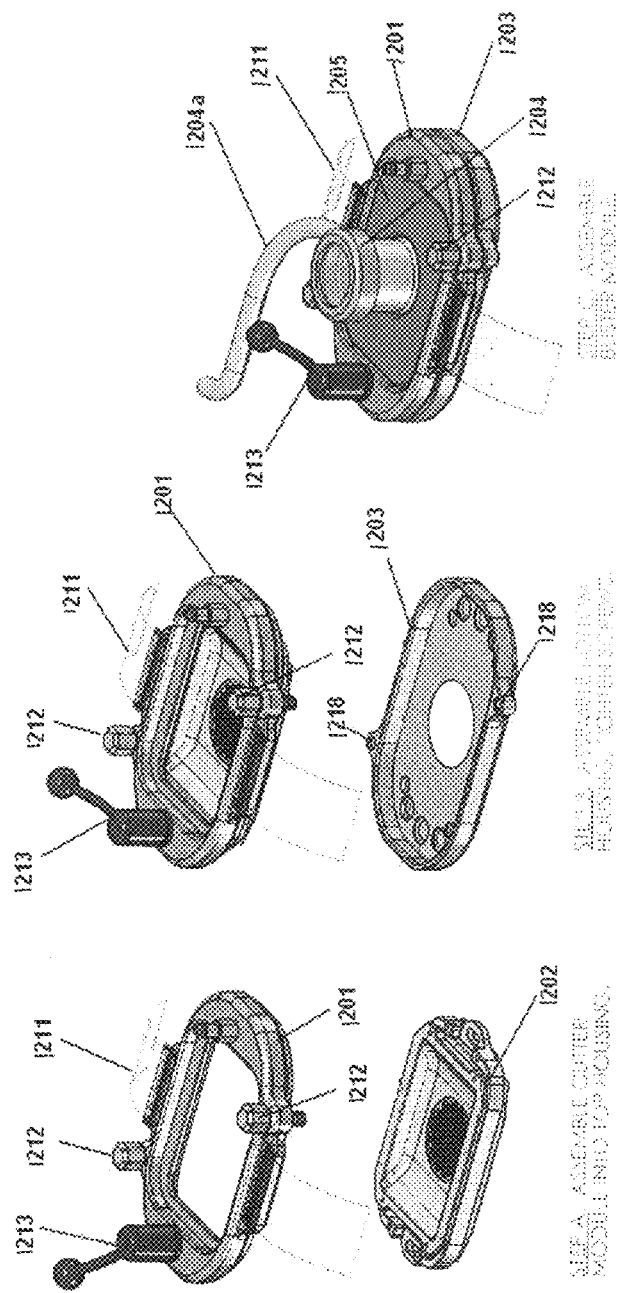

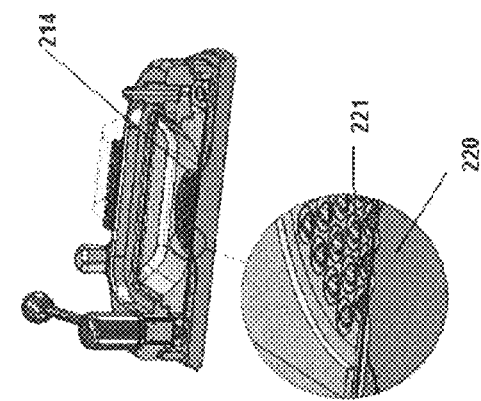
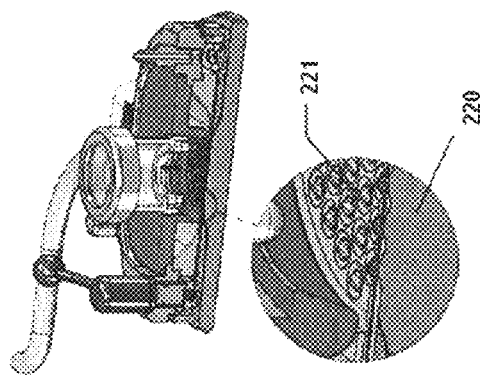
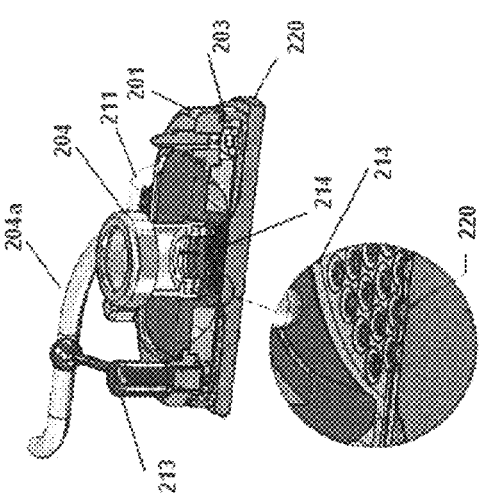
FIG. 11A
FIG. 11B
FIG. 11C

MICROBLISTER SKIN GRAFTING

REFERENCE TO RELATED APPLICATIONS

This application claims the benefit of, and priority to, U.S. patent application Ser. No. 13/346,329 filed Jan. 9, 2012, which claims the benefit of and priority of U.S. Provisional Application No. 61/567,946, filed Dec. 7, 2011.

This application also claims the benefit of, and priority to, U.S. patent application Ser. No. 13/346,318 also filed Jan. 9, 2012, which is a continuation-in-part of U.S. patent application Ser. No. 12/851,656 filed Aug. 6, 2010.

This application further claims the benefit of, and priority to, U.S. patent application Ser. No. 12/851,621 filed Aug. 6, 2010; U.S. patent application Ser. No. 12/851,703 filed Aug. 6, 2010; and U.S. patent application Ser. No. 12/851,682 filed Aug. 6, 2010.

The contents of each of the above-referenced related application are herein incorporated by reference in its entirety.

FIELD OF THE INVENTION

The present invention generally relates to devices and methods for generating and transferring skin grafts.

BACKGROUND

Skin is the largest organ of the human body, representing approximately 16% of a person's total body weight. Because it interfaces with the environment, skin has an important function in body defense, acting as an anatomical barrier from pathogens and other environmental substances. Skin also provides a semi-permeable barrier that prevents excessive fluid loss while ensuring that essential nutrients are not washed out of the body. Other functions of skin include insulation, temperature regulation, and sensation. Skin tissue may be subject to many forms of damage, including burns, trauma, disease, and depigmentation (e.g., vitiligo).

Skin grafts are often used to repair such skin damage. Skin grafting is a surgical procedure in which a section of skin is removed from one area of a person's body (autograft), removed from another human source (allograft), or removed from another animal (xenograft), and transplanted to a recipient site of a patient, such as a wound site.

As with any surgical procedure, skin grafting involves certain risks. Complications may include graft failure, rejection of the skin graft, infections at donor or recipient site, or autograft donor sites oozing fluid and blood as they heal. Certain of these complications (e.g., graft failure and rejection of the skin graft) may be mitigated by using an autograft instead of an allograft or a xenograft.

A problem encountered when using an autograft is that skin is taken from another area of a person's body to produce the graft, resulting in trauma and wound generation at the donor site. Generally, the size of the graft matches the size of the recipient site, and thus a large recipient site requires removal of a large section of skin from a donor site, leading to increased pain and discomfort and longer healing time. Additionally, as the size of the section of skin removed from the donor site increases, so does the possibility of infection.

Moreover, skin grafts are often difficult to obtain due to the tendency of the skin layer being cut to curl or fold over onto itself or the surgical instrument (e.g., dermatome), thereby comprising the integrity of the graft and making it unsuitable for use. This folding/curling tendency is particularly problematic the thinner the layer is that is being obtained, such as the epidermal layer.

While techniques have been developed for obtaining smaller micrografts that can be transferred onto a substrate for expansion prior to transplantation, such micrografts tend to clump together or can flip or fold during cutting, thereby comprising the integrity of the micrograft such that it will not properly grow on the substrate. As such, multiple cutting attempts are often necessary before a suitable, planar graft or micrograft is obtained, thereby producing multiple wound sites, leading to extreme discomfort, longer healing time, and a greater risk of infection.

Harvesting of a skin graft may be accomplished by many different techniques, and the technique used will depend on the type of graft to be harvested. A common technique to harvest a skin graft includes suction blistering. Suction blistering typically involves a heat source to warm the skin which facilitates blister formation.

The heat source of a suction blistering device can become overheated and burn out, causing inconsistent blister formation and potential harm to the patient. Thus, there is a need for a skin graft harvesting device with design features that prevent the device from overheating.

Current skin graft harvesting devices do not include means to monitor the development of suction blisters formation. Without such means, the device may be applied for overly long periods of time causing excessive discomfort or harm to the patient, or insufficient periods of time for causing blister formation. Thus, there is a need for a skin graft harvesting device with design features that allow the user to visually monitor the development of suction blisters on a patient.

A common technique for harvesting a skin graft includes creating one or more suction blisters, cutting the blister, and transferring the blister to a substrate, for example Tegaderm®. If the substrate is not sufficiently contacted with the suction blister, the blister won't transfer and will thus be unusable. As such, there is a need for a skin grafting device with design features that ensure full contact between the substrate and suction blister.

SUMMARY

The present invention provides devices for generating and harvesting a skin graft having improved design features for ensuring sufficient and consistent blister formation and reducing patient harm and discomfort.

In one aspect, the invention provides a device for generating and harvesting a skin graft having design features that prevent a heating element in the device from overheating and burning out. The device includes a head that contains a heating element for raising at least one blister, a hollow body configured for placement on a skin surface, at least one plate member and a cutting member, both integrated within the hollow body. Preferably, the heating element radiates heat between a temperature of about 100° C. to about 750° C. In a particular embodiment, the heating element radiates heat at a temperature of about 500° C. In certain aspects, the heating element radiates wavelenths ranging from about 10 nanometers to about 3000 nanometers, or any specific value within said range. Suitable materials for the heating element include, for example, nichrome wire.

The cutting member can be a second plate member integrated within the hollow body that is movable with respect to the other plate member(s) to cut the raised blister.

The plate member includes a surface that is configured for attenuating the reflection of heat emitted from the heating element. The surface configured for attenuating heat reflection includes a material that substantially absorbs the electromagnetic radiation emitted from the heating element contained within the head of the device. Suitable materials include, for example, thermoplastic polymers, including flouropolymers such as polytetrafluoroethylene. Preferably, the material is a dark colored material, such as a black, brown, purple or blue colored material. Alternatively, the surface that attenuates heat reflection can be electroplated, anodized, painted (e.g., a dark color such as black, brown, purple or blue) or abraded.

In a second aspect, the invention provides a device for generating and harvesting a skin graft having design features that allow a user, such as a clinician, to visually monitor blister formation. The device includes a head that contains a heating mechanism for raising at least one blister and at least one viewing window integrated within the head for monitoring blister formation. The device further includes a hollow body configured for placement on a skin surface, at least one plate member and a cutting member, both integrated within the hollow body. The cutting member can be a second plate member integrated within the hollow body that is movable with respect to the other plate member(s) to cut the raised blister.

The viewing window is preferably made of a substantially transparent material, such as an optical polymer, glass or crystal. Such materials may include an anti-fog treatment, anti-scratch coating, or anti-glare coating. In certain aspects, at least a portion of the viewing window includes a magnification lens. In another aspect, the viewing window can include at least one calibration mark for monitoring blister formation. The viewing window may simultaneously serve as an optical shield and attenuate the entrance of ambient light.

In a third aspect, the invention provides a device for generating and harvesting a skin graft having design features for monitoring blister formation that include a gauge integrated within the body of the device. The device includes a head comprising a mechanism for raising one or more blisters, a hollow body configured for placement on skin, a plate member and a cutting member integrated within the hollow body. The cutting member can be a second plate member integrated within the hollow body that is movable with respect to the other plate member(s) to cut the raised blister.

The plate member includes one or more holes through which the one or more blisters are raised, and a gauge integrated within the plate for monitoring blister formation within the one or more holes. The holes have a depth substantially equal to the thickness of the plate member. The gauge is proximal to one or more of the holes through which the blisters are raised. In certain aspects, the gauge is a counter-bore within one or more of the holes in the plate member. The counter bore can be about one-half to three-quarters of the depth of the hole. Alternatively, the gauge is a calibration mark proximal to one or more of the holes in the plate member. For example, the calibration mark can be laser etched or painted onto the plate next to one or more holes, or on the inner wall of one or more holes within the plate.

In a fourth aspect, the invention provides a device for generating and harvesting a skin graft having design features for improving heat transfer to facilitate blister formation. Such devices include a head that contains a heating mechanism for raising at least one blister, and a transparent or translucent surface distal to the heating mechanism for transferring heat from the heating mechanism to the body of the device. The device further includes further includes a hollow body configured for placement on a skin surface, at least one plate member and a cutting member, both integrated within the hollow body. The cutting member can be a second plate member integrated within the hollow body that is movable with respect to the other plate member(s) to cut the raised blister.

The transparent or translucent surface is preferably made of a material that allows light having a wavelength between about 10 nanometers to about 3000 nanometers to be transmitted therethrough (e.g., about 180 nm to about 2500 nm). Suitable materials include, for example, crystalline materials such as, sapphire, quartz, silicon, garnet, sillenite, fused quartz, titanium dioxide, zinc selenide, calcium fluoride, barium fluoride, zinc sulphide, caesium iodide, germanium, thallium bromo-iodide, lithium fluoride, magnesium fluoride, potassium bromide, sodium chloride, or strontium fluoride; or glass materials such as silica glass, fused silica, fluoride glass, aluminosilicate glass, phosphate glass, borate glass, chalcogenide glass, or a polymer glass.

In certain aspects, the head of the device includes two transparent or translucent surfaces distal to the heating mechanism, configured such that the two surfaces contain an airspace in between. The two surfaces can be made of the same material, or different materials. In a particular embodiment, the two surfaces are both a glass material.

In a fifth aspect, the invention provides a device for generating and harvesting a skin graft having design features for ensuring the capture and transfer of blisters onto a substrate. Such devices include a mechanism for raising at least one blister, a hollow body configured for placement on skin, at least one plate member integrated within the body and including at least one hole through which the blister is raised, a substrate removably coupled to the plate member, and a substrate compression mechanism movably coupled to the body. The substrate compression mechanism includes an actuator member coupled to a compression member. Actuation of the compression mechanism removably couples the compression member onto the substrate to ensure full contact between the substrate and the raised blister.

The device further includes a cutter member integrated within the body for cutting the blister. The cutting member can be a second plate member integrated within the hollow body that is movable with respect to the other plate member(s) to cut the raised blister. The device is configured such that the blister is attached to the substrate upon cutting the blister.

The compression member is movably coupled to the hollow body via an axle, a hinge, or similar mechanism that allows the compression member to be removably applied to the substrate. The actuation member can be a handle coupled to the compression member to facilitate application of the compression member to the substrate.

The compression member can be substantially the same size and shape as the substrate. For example, the compression member can be substantially square or rectangular in shape having the same dimensions as the substrate. Alternatively, the compression member can be cylindrical in shape and configured to roll along the surface of the substrate when actuated. For example, a cylindrical compression member can be configured to rotate about the longitudinal axis of a movable arm, whereby actuation of the arm in a horizontal direction translates into rotation of the compression member about the arm to roll the cylindrical member across the substrate The compression member can be made of any substantially solid material, such as any elemental metal, metal alloy, glass, crystal or polymer. The compression member is preferably reusable. However, in certain aspects, the compression member can be disposable.

The present invention also provides devices for producing skin graft material and methods for manufacturing components for use in devices for producing skin graft material. The invention provides manufacturing methods for creating plates, preferably metallic plates, for use in preparing skin grafts. Manufacturing methods as described herein are useful to fabricate plates for use in devices as described below.

Methods of the invention result in plates for use in harvesting skin grafts produced by the application of blistering to a donor site. Methods of the invention involve the generation of a plurality of plates having substantially planar mating surfaces from a material, preferably a metallic material. Preferably, at least one of the plates has substantially uniform thickness throughout the plate. In certain embodiments, each of the plurality of plates has a substantially uniform thickness throughout each plate and/or with respect to each other. The plurality of plates can be generated from the same material, or different materials.

A plurality of coupling members for coupling the plurality of plates together in a stacked configuration are preferably generated from the same material as at least one or more of the plate members such that the coupling members are substantially uniform in thickness with respect to each other and the at least one plate member, and contain substantially the same planar surface with respect to each other and the at least one of the plate member.

According to one aspect of the invention, a plurality plates are manufactured from the same sheet stock of material. For example, a single sheet stock of material is divided into a plurality of sections having uniform shape and size with respect to each other, each section corresponding to an individual plate member. At least one opening (e.g. hole or slot) is formed in each of the plate members such that the openings are in concentric alignment when the plate members are assembled in a stacked configuration.

In certain embodiments, the plurality of coupling members for coupling the plate members together in a stacked configuration are also formed from the same sheet stock from which the plate members are generated. Fabrication of the coupling members does not substantially change the planar surface of the plates, such that the plates are stackable in a form-fitting manner and subsequently movable with respect to one another. The coupling members are disposed between the plate members. The coupling members can be disposed along the outer surface of the plate members, or between one or more openings (e.g., holes or slots) formed within each plate. In certain aspects, the coupling members form a frangible section between the plates that is broken upon movement of the plates with respect to each other in operation, as described below. Optionally, a portion of the plate material at or around the site of the coupling is removed to accommodate at least a portion of the coupling member and forming a depression at or around the frangible section.

Preferred methods for fabricating plates for use in skin graft generator devices involve obtaining one or more plates of substantially uniform thickness and forming holes in the plates that align upon stacking Plates preferably have integrated coupling members that do not substantially alter the thickness of the plates and allow for coupling of the plates via a frangible linkage. In operation, the plates are moved in order to break the coupling and to cut a graft from a skin blister formed by the device into which the plates are placed. Preferably, there are three plates, with a central plate having openings (e.g., holes or slots) that form a cutting surface. In operation, the plates are moved such that the cutting surface interacts with blisters protruding through aligned openings in a plate below. Ideally, coupling members are substantially uniform in shape and size and the frangible linkage is laser welded, but may also be a mechanical stamp, a mechanical punch, a weld, epoxy or other adhesive, formed via mechanical compression, snap fit, tongue and groove, post and bar, frangible pin or other known connectors.

Plates manufactured as described herein are useful in a device for reliably generating skin micrografts in a single attempt. A device of the invention is configured to generate a plurality of substantially planar micrografts in a single cutting motion. Devices of the invention are further capable of simultaneously transferring generated micrografts onto a substrate. Devices of the invention are particularly well-suited for generating and transferring a plurality of substantially planar epidermal micrografts.

In certain aspects, the invention provides a device that includes a body having a bottom surface configured for placement on skin, a mechanism for raising at least one blister on the skin, and a cutter configured to cut formed blisters in order to produce grafts for transplantation.

The cutter may include a plurality of plates, each plate having an array of openings (e.g., an array of holes or slots). In certain embodiments the openings are substantially cylindrical in shape. The openings in the arrays are of a size to facilitate production of a plurality of grafts from formed blisters. The openings can range in size from about 1 mm to about 12 mm diameter. In a particular embodiment, the openings are no greater than about 2 mm in diameter.

At least one of the plates is movable relative to the other plates. The plurality of plates in the cutter are configured such that a substantially planar graft (i.e., one that is not curled, folded or clumped) is produced.

The mechanism for raising the at least one skin blister can be a vacuum source, a heat source (e.g., a light source or warm air), or a combination of both.

Once the blister(s) is generated, a removable substrate is applied to the blister simultaneously transfer/retain the blister upon cutting. The substrate can include an adhesive to facilitate attachment of the blister to the substrate.

The device of the invention may further include a strap for securely coupling the device against a skin surface such as the inner thigh or buttocks. The strap may be adjustable in size, or may be a fixed size. In certain embodiments, the strap is a belt/loop fastener. In other embodiments, the strap is a metal or plastic cuff configured to for attachment around the upper thigh.

In another aspect, the invention provides a device for obtaining a skin graft that includes a hollow body having a bottom surface configured for placement on skin, a mechanism for raising at least one blister, and a plurality of plates, each plate including an array of holes configured so as to maintain the integrity of a graft produced by cutting the raised blister.

In certain embodiments the openings in the hole array of each plate are substantially cylindrical in shape and are of a size to facilitate production of a substantially planar graft. For example, the holes can range in size from 1 mm to a 12 mm diameter, or any specific value in between such range. In a particular embodiment, the openings in the hole arrays are no greater than about 2 mm in diameter.

The mechanism for raising the at least one skin blister can be a vacuum source, a heat source (e.g., a light source or warm air), or a combination of both.

A substrate removably connected to the body of the device directly contacts the generated blister(s) such that upon cutting of the blister, the cut portion of skin is attached to the substrate. The substrate can include an adhesive to facilitate attachment of the blister to the substrate.

The device may further include a strap for securely coupling the device against a skin surface such as the inner thigh or buttocks. The strap may be adjustable in size, or may be a fixed size. In certain embodiments, the strap is a belt/loop fastener. In other embodiments, the strap is a metal or plastic cuff configured to for attachment around the upper thigh.

In yet another aspect, the invention provides a cutting device that includes a first plate having at least one opening, a second plate having at least one opening, the second plate being attached to said first plate, and a third plate having at least one opening, the third plate being attached to said second plate. At least one of the plates is movable with respect to the other plates. For example, the second plate may be movable with respect to the first and/or third plates. In other embodiments, the third plate may be stationary in operation with respect to at least one of said first and second plates. In certain embodiments, the second plate is attached to said first plate via at least one frangible section. The frangible section is broken upon movement of said plates with respect to each other. The frangible coupling of the plate members to each other can be accomplished using a mechanical stamping technique, a mechanical punch technique, spot welding, an epoxy, an adhesive, mechanical compression, a snap-fit assembly, a tongue and groove assembly, a post and bar assembly, a frangible pin, or any combination thereof.

At least one of the openings in the first, second or third plate defines a cutting surface. In certain embodiments, the cutting surface on one of the plates engages a cutting surface on at least one other of said plates in operation (i.e., when at least one of the plates is moved with respect to the other plates). In certain embodiments, the opening in at least one of the plates moves with respect to the openings in at least another of said plates, thereby to perform a cutting action.

In certain embodiments, the first, second and third plates each include a plurality of openings that are concentrically aligned with respect to each other in a home position, and offset with respect to each other in an operating position (i.e., when at least one of the plates moves respect to the other plates).

In yet another aspect of the invention, two part systems for harvesting of skin microblisters are disclosed. The two parts are a harvester that is adapted for attachment to a target region of skin and head which delivers negative pressure and/or heat to at least portions of the skin engages by the harvester.

More specifically, the head is adapted for coupling to a cutting body ("harvester") that is disposable on a patient's skin and further adapted for coupling to a vacuum source, the head further providing a sealing surface to engage with a mating surface on the cutting body such that, when the head is engaged with the cutting body on a patient's skin, a evacuated chamber is formed over a target region of skin; and, preferably, a heating element for raising the temperature of the target region of skin and, further preferably at least one viewing window for observing blisters formed by heating the skin in the evacuated chamber.

In certain embodiments the window is formed on at least one side surface of the head at a non-parallel angle to the patient skin so skin blisters being raised in the chamber can be more readily observed. The head can further include at least one light source, such as a light emitting diode (LED) for illuminating skin blisters as they are being raised.

The viewing window is preferably composed of a substantially transparent material, such as an optical polymer, an optical glass, and an optical crystal and at least a portion of the viewing window further comprises a magnification lens, e.g., that magnifies objects at a magnification ranging from about 2× to about 100×. The viewing window can also include one or more materials selected from an anti-fogging material, an anti-scratch coating, and an anti-glare coating and, preferably, is formed of a heat resistant material. The viewing window comprises an ocular shield configured for attenuating entrance of ambient light.

The head can further include a heating element that is a resistive electrical heating element. The head can also include at least one temperature measuring element, such as a thermistor, for measuring the temperature of the skin or evacuated chamber.

The harvester is configured for placement on a target region of a patient's skin and further adapted to form a sealing engagement with a head that provides negative pressure to the target region such that the target region of skin is embraced within an evacuated chamber In one embodiment, the harvester further includes at least one alignment plate having a plurality of holes through which skin blisters can be raised in the presence of negative pressure; and a cutting plate having at least one cutting surface for cleaving skin blisters after they are formed within the chamber.

At least a part of the harvester e.g., a top alignment plate, can be formed of a radiation absorbing material, such as a fluoropolymer surface coating or layer to enhance heating of the skin.

In another preferred embodiment, the harvester includes a top alignment plate and a bottom alignment plate and the cutting plate is disposed therebetween. The top and bottom alignment plates can be joined together by a plurality of vertical posts that pass through slots in the cutting plate to maintain the fixed position of the top and bottom plates relative to each other while permitting movement of cutting plate. The top plate, bottom plate and cutting plate can each have a plurality of holes that are adapted to be concentrically aligned to facilitate blister formation. In certain embodiments, the holes of the top plate are larger than the holes of the bottom plate.

The cutting plate can includes a plurality of holes suitable for concentric alignment with holes in the alignment plate in a first position to facilitate blister formation and a plurality of cutting surfaces suitable for cleaving blister in a second position.

The harvester can further include an actuator for moving the cutting plate from the first position to the second position and the actuator can configured to also at least partially retract the cutting plate following blister cleavage.

These and other aspects of the devices of the invention are described in the figures, description and claims that follow. While several improved design features have been individually described, such features are not mutually exclusive of each other. Any combination of design features disclosed herein can be used integrated into the devices of the invention. These design features and other aspects of the devices of the invention are described in the figures, description and claims that follow.

BRIEF DESCRIPTION OF THE DRAWINGS

FIG. 3 panels A-B is a drawing showing a device of the invention for raising a suction blister.

FIG. 4 panels A-D show different devices of the invention for raising a suction blister.

FIGS. 8A-8C are schematics depicting the assembly procedure of the components depicted in FIGS. 7A and 7B.

FIGS. 11A-11C are schematics depicting the blister generation steps using the device mode depicted in FIG. 10A.

DETAILED DESCRIPTION

The present invention generally relates to a single device that can raise a blister (e.g., a suction blister) and cut the raised blister, i.e., a blister raising device integrated with a cutting member. Such devices are useful for harvesting skin grafts.

Figure 2:
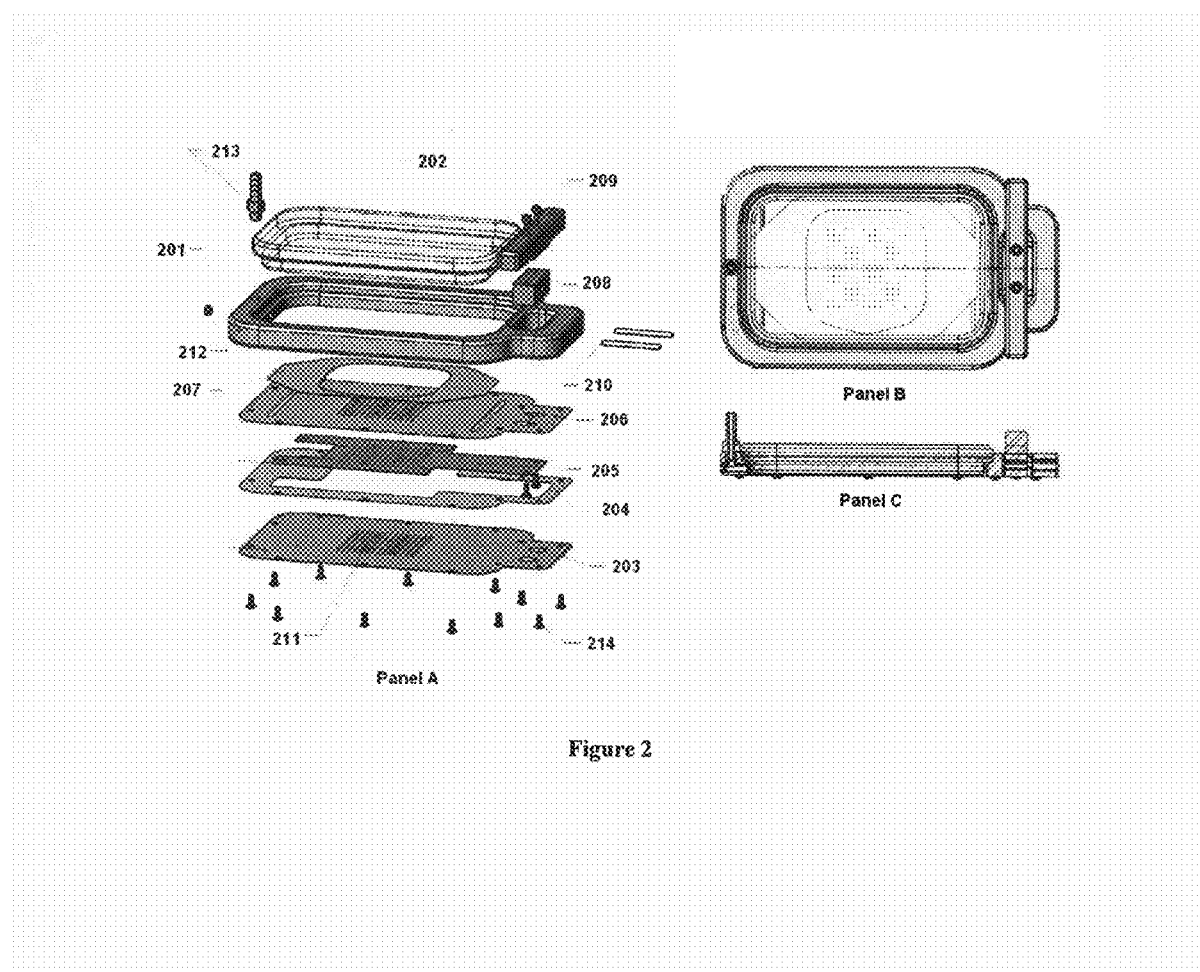
FIG. 2 panels A-C are schematics showing a device for generating and harvesting a plurality of micrografts. Panel A provides an exploded view of the device. Panel B provides a top view of the assembled device. Panel C provides a side view of the assembled device.

In certain embodiments, a device as shown in FIG. 2 panels A-C is used to raise and cut a plurality of skin grafts. Device 200 includes a frame 201 and a lid 202. Fitted into the frame is a bottom plate 203, a cutter grid plate 204, a cutter plate 205, and a top plate 206. The bottom plate 203, the cutter plate 205, and the top plate 206, each include a hole array 211. Once assembled, the hole array 211 of each of plates 203, 205, and 206 are aligned. The size of the holes in the hole array will depend on the size of the graft needed, with larger holes being used to produce larger grafts. A first substrate 207 interacts with the top plate 206 and will receive the harvested grafts.

Device 200 further includes an actuation block 208, actuation bar 209, and actuation block guides 210. Actuation components 208, 209, and 210 control movement of the cutter plate 205. The frame 201 includes a vacuum stop 212 and the lid 202 includes a suction hole barb 213. Once assembled, the frame 201 and lid 202 are arranged such that the vacuum stop 212 and the suction hole barb 213 are aligned with each other (FIG. 2 panel B). A vacuum source is then connected to the device 200 such that negative pressure can be generated within the device. The device 200 can be held together by clamp screws 214. Device 200 may also include a heating element.

To produce and harvest the plurality of skin grafts, device 200 is placed on a donor site, such as an inner thigh of a patient. The vacuum source is turned on, producing negative pressure within device 200. The negative pressure causes the skin to be pulled toward lid 202, with a plurality of different portions of skin being pulled through each hole array 211 in each of plates 203, 205, and 206. Such action results in generation of many microblisters. Once the microblisters are raised, actuation components 208, 209, and 210 are engaged to move cutter plate 205. The movement of cutter plate 205 disrupts the alignment of the hole arrays 211 in each of plates 203, 205, and 206, and results in cutting of the microblisters. The cut microblisters are captured on the first substrate 207 that is above top plate 206. In this manner, there is provided a spaced apart array of micrografts. The amount of negative pressure applied, the amount of time the vacuum is maintained, and/or the depth of the holes in plate 206 (i.e., the plate thickness) determine what type of graft will be harvested, e.g., epidermal graft, split thickness graft, or full thickness graft. Generally, each micrograft will have a lateral dimension of less than about 2 mm e.g., 100 to 2000 microns.

Another aspect of the invention provides a device for obtaining a single skin graft. Such devices of the invention include a hollow body having a distal end configured for placement on skin, a mechanism for raising a blister, and a cutter integrated in the body for cutting the blister produced on the skin.

A gauge for monitoring blister formation can be incorporated within one or more plates 203, 205, and 206. The gauge is preferably proximal to one or more holes of hole array 211 through which the blisters are formed. For example, the gauge can be located on the plate next to one or more holes of hole array 211, or on an inner wall of one or more holes of hole array 211. The gauge can be configured to provide minimum indicator of a sufficient height or dimension for a blister to be cut, and/or a maximum indicator of a sufficient blister dimension to avoid excessive patient discomfort by application of the device beyond a necessary period of time.

Each hole within the hole array has a depth substantially equal to the thickness of the plate. In certain embodiments, the gauge is a counterbore through one or more of the holes within hole array 211. The counter bore serves as a marker to indicate to the user (e.g., clinician) when the blister has reached a dimension sufficient to be cut. The counterbore can be approximately one-half to three-quarters of the depth of the hole as measured from the bottom or distal-most surface of the plate (i.e., the surface closest to the skin). For example, if the plate is 0.3 inches thick, the counter bore is 0.15 inches to 0.225 inches, as measured from the bottom or distal-most surface of the plate.

Alternatively, the gauge can be one or more calibration marks located proximal to or within one or more holes through which the blisters are raised. For example, the calibration marks can be one or more lines having a known length that are drawn, painted or etched onto the surface of the plate proximal to one or more of the holes. For example the one or more lines have a length of about 0.1 mm, about 0.2 mm, about 0.3 mm, about 0.4 mm, about 0.5 mm, about 1.0 mm, about 2.0 mm, about 3.0 mm, about 4.0 mm, about 5.0 mm, about 6.0 mm, about 7.0 mm, about 8.0 mm, about 9.0 mm, about 10.0 mm, about 11.0 mm, about 12.0 mm, about 13.0 mm, about 14.0 mm, about 15.0 mm, about 16.0 mm, about 17.0 mm, about 18.0 mm, about 19.0 mm, about 20.0 mm, about 21.0 mm, about 22.0 mm, about 23.0 mm, about 24.0 mm, or about 25.0 mm. Alternatively, at least two calibration marks can be drawn, painted or etched onto the surface of the plate proximal to one or more of the holes, and the distance between the at least two calibration marks can be a known length, for example about 0.1 mm, about 0.2 mm, about 0.3 mm, about 0.4 mm, about 0.5 mm, about 1.0 mm, about 2.0 mm, about 3.0 mm, about 4.0 mm, about 5.0 mm, about 6.0 mm, about 7.0 mm, about 8.0 mm, about 9.0 mm, about 10.0 mm, about 11.0 mm, about 12.0 mm, about 13.0 mm, about 14.0 mm, about 15.0 mm, about 16.0 mm, about 17.0 mm, about 18.0 mm, about 19.0 mm, about 20.0 mm, about 21.0 mm, about 22.0 mm, about 23.0 mm, about 24.0 mm, or about 25.0 mm. As the blister is formed, the lateral dimension of the blister can be compared to the one or more calibration marks to gauge when the blister is ready to be cut.

In yet another embodiment, the calibration marks may be one or more markings that are drawn, painted or etched onto the inner wall of one or more holes within hole array 211 of the plates. Such markings can indicate a minimum depth within the hole that is sufficient for a blister to be cut, and a maximum level for sufficient blister formation to avoid excessive patient discomfort by application of the device beyond a necessary period of time.

In certain embodiments, a device as shown in FIG. 3 panel A is used to obtain a skin graft. Device 400 includes a hollow body 401 and a mechanism for raising a blister 402. Hollow body 401 includes a distal end 403 that is configured for placement on the skin. Such a distal end may include an orifice plate 404. Orifice plate 404 determines the size and the shape of the blister or blisters that will be raised. Orifice plate 404 may be any shape or size and will depend on the blister to be raised. Generally, the diameter or lateral dimension of the blister may be from about 6 mm to about 12 mm, although larger or smaller blister sizes may be used.

The mechanism for raising a blister may be a vacuum component, a heating component, or a combination thereof. An exemplary heating component is a light source. In a particular embodiment, mechanism 402 is a combination of a vacuum component and a heating component.

The hollow body 401 further includes a cutter 405, which includes cutter plate 406 and a hole 407 (FIG. 3 panel B). Device 400 further includes an actuation block 408, actuation bar 409, and actuation block guides 410. Actuation components 408, 409, and 410 control movement of the cutter 405.

Blister formation is accomplished by attaching the distal end 403 of hollow body 401 to donor site of a patient, such as an inner thigh of a patient. Hook and loop fastener straps may be used to keep the device in place. The heating component of blister raising mechanism 402 provides a slight warming of orifice plate 404, which is in direct contact with the patient's skin surface. The application of a moderate negative pressure to the chamber interior from the vacuum component of blister raising mechanism 402, results in the patient's skin being gently drawn through the opening in orifice plate 404. The result is a blister or blisters, approximately the size of the opening in orifice plate 404. The produced blister may be fluid-filled or may not contain any fluid, i.e., a blister having air within. The skin and blister area is generally not damaged and patient discomfort is minimal.

The cutter 405 is positioned in hollow body 401 such that upon raising the blister, at least a portion of the blister protrudes through hole 407 in cutter plate 406. The actuation components 408, 409, and 410 are engaged to move cutter plate 406. The movement of cutter plate 406 disrupts the alignment of hole 407 with the other components of device 400, and results in cutting of the raised blister.

Preferably, the blister raising mechanism 402 is capable of emitting heat ranging between about 100° C. to about 750° C. (e.g., about 500° C.). In certain aspects, the blister raising mechanism 402 emits electromagnetic radiation having a wavelength ranging between about 10 nm and about 3000 nm. In certain aspects, electromagnetic radiation emitted from blister raising mechanism 402 is reflected off one or more of the surfaces within the device, back to mechanism 402, causing it to overheat and burnout. To prevent overheating of mechanism 402, at least one plate of plates 203, 205, and 206 and/or orifice plate(s) 404 can include at least one surface configured for attenuating the reflection of electromagnetic radiation emitted from mechanism 402. Preferably such surface is the surface facing mechanism 402 when the device is fully assembled.

For example, at least one surface of one or more of plate members 206, 205, 203 and/or orifice plate 404 can be coated with a material that substantially attenuates reflection of the electromagnetic radiation (e.g., by absorbing) emitted from mechanism 402. Suitable materials include, for example, a thermoplastic polymer coating. In a particular embodiment, the thermoplastic polymer is a fluoropolymer such as polytetrafluoroethylene. Preferably, the coating material is a dark color such as a substantially black, brown, blue or purple color.

Alternatively, one or more of plate members 206, 205, 203 and/or orifice plate 404 can be anodized, electroplated or painted a dark color such as black, brown, blue or purple to attenuate the reflection (e.g., absorb) of electromagnetic radiation emitted from mechanism 402.

In yet another embodiment one or more of plate members 206, 205, 203 and/or orifice plate 404 can be abraded, scuffed, brushed, or the like, to minimize or remove a glossy or shiny surface appearance in order to attenuate reflection of electromagnetic radiation from mechanism 402.

FIG. 4 panel A shows a device 500 that further includes a chamber 511 for capturing the cut blister. Chamber 511 is positioned in hollow body 501 and above cutter 505. Chamber 511 may be removable from device 500. Chamber 511 may include multiple configurations. For example, chamber 511 may include a retractable bottom. The bottom is in an open position when chamber 511 is inserted into hollow body 501. In the open position, chamber 511 is able to receive the cut blister. Once the cut blister is in chamber 511, the bottom of the chamber is closed, capturing the blister in chamber 511. Chamber 511 may then be removed from device 500.

In another embodiment, chamber 511 includes a substrate 512 (FIG. 4 panel C). In this embodiment, device 500 is configured such that substrate 512 is positioned in chamber 511 so that upon raising the blister, a portion of the blister contacts the substrate and becomes attached to the substrate. Cutter 505 then cuts the blister, and the cut blister becomes attached to the substrate 512 in chamber 511. Chamber 511 is then removed from device 500, and substrate 512 may be removed from chamber 511. In other devices, a vacuum, instead of a substrate, is used to hold the cut blister within the chamber.

In certain embodiments, device 500 does not use a chamber, rather a substrate 512 is directly integrated with device 500 in order to capture the cut blister (FIG. 4, panel D). Once captured, substrate 512 having an attached cut blister may be removed from device 500.

In certain embodiments, the device 500 includes a substrate compression mechanism for pressing the substrate against the blister to ensure that the entire blister surface contacts the substrate 512. Full contact between the entire blister surface and the substrate ensures transfer of the blister onto the substrate when the blisters are cut. In certain embodiments, the compression member is movably coupled to an exterior surface of the hollow body and actuated by an actuation member coupled to the compression member.

The compression member can be a plate having approximately the same size and shape as substrate 512. The plate can be coupled to the hollow body via a hinged mechanism or axle member and is actuated by an extension arm or handle fixedly attached to the plate. The extension arm/handle is engineered to apply at least about 2x, at least about 3x, at least about 4x, at least about 5x, at least about 6x, at least about 7x, at least about 8x, at least about 9x, at least about 10x, at least about 15x, at least about 20x, at least about 25x, at least about 30x, at least about 35x, at least about 40x, at least about 50x, at least about 75x, at least about 100x the pressure applied to the extension arm/handle onto the plate.

Alternatively, the compression mechanism can be a cylindrical roller disposed about an actuation arm that defines a longitudinal axis. Movement of the arm in a lateral direction translates into rotational movement of the cylinder about the longitudinal axis of the arm, such that the cylinder is rolled across the surface of the substrate 512 to press the substrate against the blisters.

The compression member and/or actuation member preferably reusable. Alternatively, the compression member and/or actuation member are made of a disposable material. Materials for the construction of the compression plate or cylinder can be any substantially solid material such as an elemental metal, a metal alloy, a glass, a crystal, or a polymer. In certain embodiments, the compression member and/or actuation member are made of titanium or stainless steel.

Figure 5:
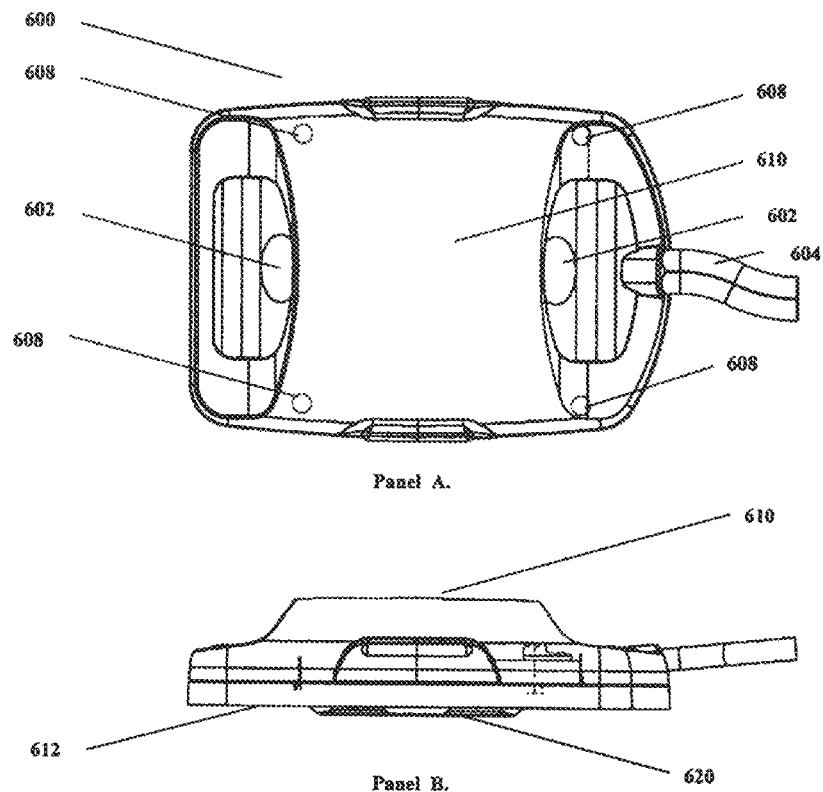
FIG. 5 panels A-B show schematics of head of a device according to the invention. Panel A provides a top view of the head. Panel B shows a side view of the head.
Figure 6:
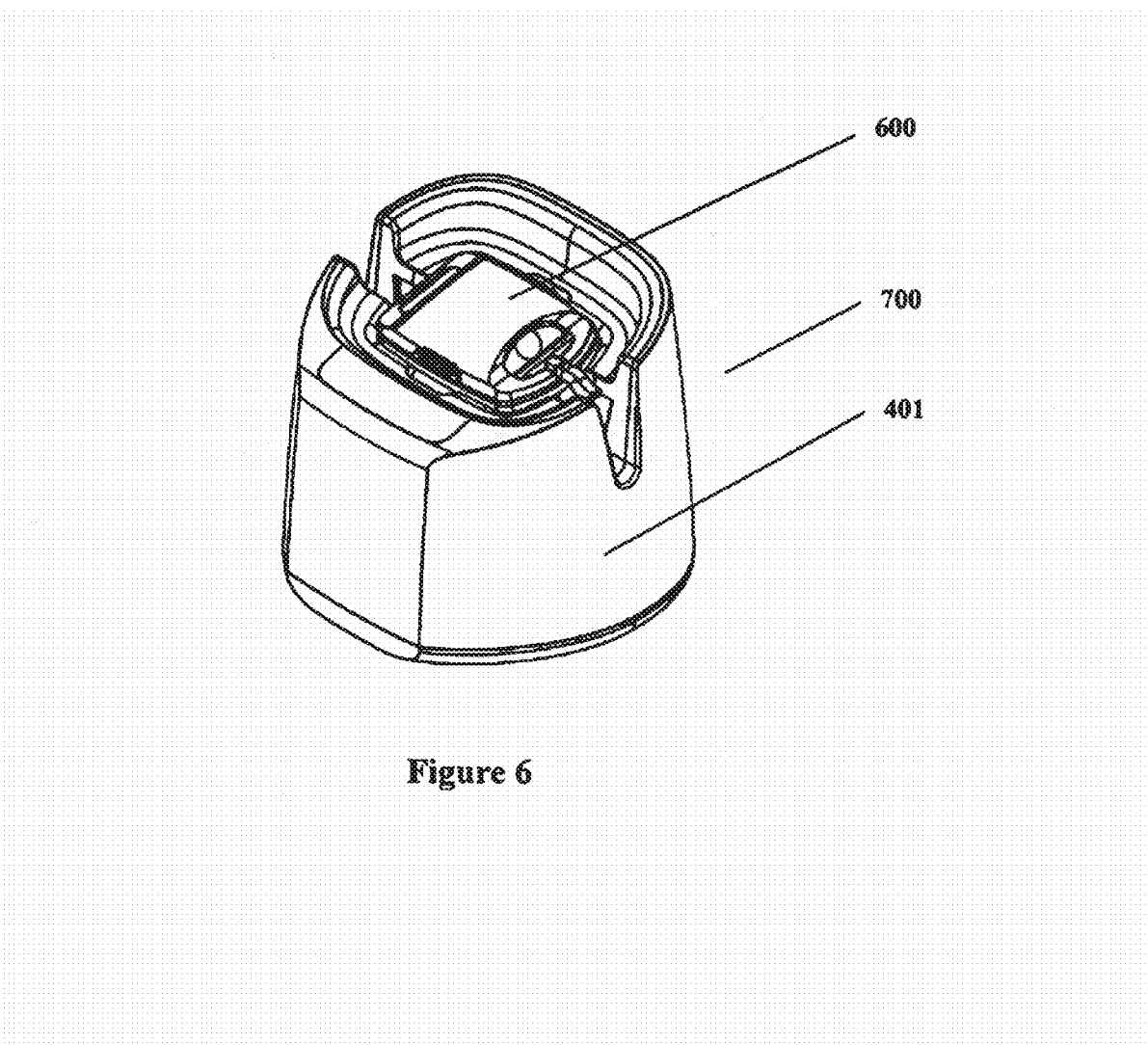
FIG. 6 provides a diagram showing an external schematic of a device with a head coupled to a hollow body.

In certain embodiments, the devices according to the invention include a head portion that can be removably coupled with the hollow body 401 of the device. FIG. 5 shows an exemplary embodiment of a removable head 600 that includes a blister raising mechanism 402 (e.g., a heating element) for raising a suction blister. The head 600 includes a topmost, proximal portion 610, and a distal portion 620 that couples with the hollow body of the device. The head 600 is coupled to the hollow body 401 via holes 608. After attachment of head 600 to the hollow body 401, a vacuum source can be attached to suction tubing 604 to generate negative pressure within the hollow body of the device. FIG. 6 shows head 600 coupled to hollow body 401 (collectively 700).

In certain embodiments, the head device includes one or more viewing windows 602. The viewing windows are located to provide optimal viewing of blister formation within the hollow body of the device. As shown in FIG. 5, a plurality of viewing windows 602 can be integrated within the head 600 to allow for alternative views of blister formation, or allow more than one user to monitor the development of the blisters. In certain embodiments, an ocular shield circumscribes the viewing lens such then when the user is viewing blister formation, the shield attenuates entrance of ambient light into the viewing lens.

The viewing window 602 can be made of any transparent material. In preferred embodiments, the viewing window 602 is comprised of optical quality material, for example an optical polymer, an optical glass, or an optical crystal. Such materials can further include one or more of an anti-fogging material, an anti-scratch coating, or an anti-glare coating, located on either the or both the interior surface, the exterior surface, or both.

In certain embodiments, the viewing window is made of a heat resistant optical polymer, optical glass, or optical crystal to prevent warping or distortion from the heating element of the blister raising mechanism 402 within the head 600.

At least a portion of the viewing window 602 can further include a magnification lens to facilitate viewing of the blisters during formation. The magnification power of the lens can be at least about 2x, at least about 3x, at least about 4x, at least about 5x, at least about 6x, at least about 7x, at least about 8x, at least about 9x, at least about 10x, at least about 15x, at least about 20x, at least about 25x, at least about 30x, at least about 35x, at least about 40x, at least about 50x, at least about 75x, at least about 100x.

In still other embodiments, the viewing window 602 can include one or more calibration marks etched or painted on the viewing window 602 for monitoring blister formation. Where the viewing window 602 includes a magnification lens, the calibration marks can be calibrated to the magnification power of the lens to approximate the actual dimensions of the forming blister, such as the actual height, the actual diameter, or both. When the desired blister size is formed as gauged by the calibration marks, the blisters are cut.

As previously described, the head 600 can include a mechanism for raising a blister 402. Such mechanism typically includes a heating element, such as nichrome wire, and is located in the topmost, proximal portion 610 of head 600.

In certain embodiments of invention, head 600, includes a transparent or a translucent surface 620 forming the distal side 612 of the head 600 (i.e., distal to the heating element). The transparent or translucent surface is made of a material that facilitates the transmission of electromagnetic radiation emitted from the heating element within head 600 to one or more plate members incorporated within the hollow body, thereby warming the plate members and subsequently the skin surface.

In certain aspects, the transparent or translucent surface is made of material that allows light having a wavelength between about 10 nanometers to about 3000 nanometers to be transmitted through the surface. Suitable materials for transmission of light within such range includes, for example, crystalline materials such as sapphire, quartz, silicon, garnet, sillenite, fused silica, fused quartz, titanium dioxide, zinc selenide, calcium fluoride, barium fluoride, zinc sulphide, caesium iodide, germanium, thallium bromo-iodide, lithium fluoride, magnesium fluoride, potassium bromide, sodium chloride, or strontium fluoride. The crystalline material can polarized.

Other suitable materials include glass such as silica glass, fluoride glass, aluminosilicate glass, phosphate glass, borate glass, chalcogenide glass, or polymer glass. The glass can be polarized.

In certain aspects, the head 600 includes two transparent or translucent surfaces 620 forming the distal side 612 of head 600. The two plates surfaces are in a stacked configuration with an airspace in between them. The airspace between the transparent or translucent surfaces is about 0.1 mm, about 0.2 mm, about 0.3 mm, about 0.4 mm, about 0.5 mm, about 0.6 mm, about 0.7 mm, about 0.8 mm, about 0.9 mm, about 1.0 mm, about 2.0 mm, about 3.0 mm, about 4.0 mm, about 5.0 mm, about 6.0 mm, about 7.0 mm, about 8.0 mm, about 9.0 mm, about 10.0 mm, about 11.0 mm, about 12.0 mm, about 13.0 mm, about 14.0 mm, about 15.0 mm, about 16.0 mm, about 17.0 mm, about 18.0 mm, about 19.0 mm, about 20.0 mm, about 21.0 mm, about 22.0 mm, about 23.0 mm, about 24.0 mm, or about 25.0 mm.

The two transparent or translucent surfaces can be the same materials, or different materials. For example, the two surfaces can both be made of a glass or crystalline material. Alternatively, one of the surfaces is a glass material, while the other surface is a crystalline material.

In another aspect, the invention relates to an integrated device for generating micrografts and transferring micrografts. More specifically, the invention relates to a device for generating substantially planar micrografts and for preparing a surgical dressing to facilitate presentation of the micrografts to a patient in need thereof. The device of the invention can be used to prepare any type of skin graft, such as an epidermal skin graft, a split thickness graft, or a full thickness graft. However, the device of the invention is particularly well suited for preparing skin grafts including only or substantially only the epidermal layer of skin. The device of the invention can be used for autografts, allografts, or xenografts. In preferred embodiments, the grafts are autografts.

Figure 7A:
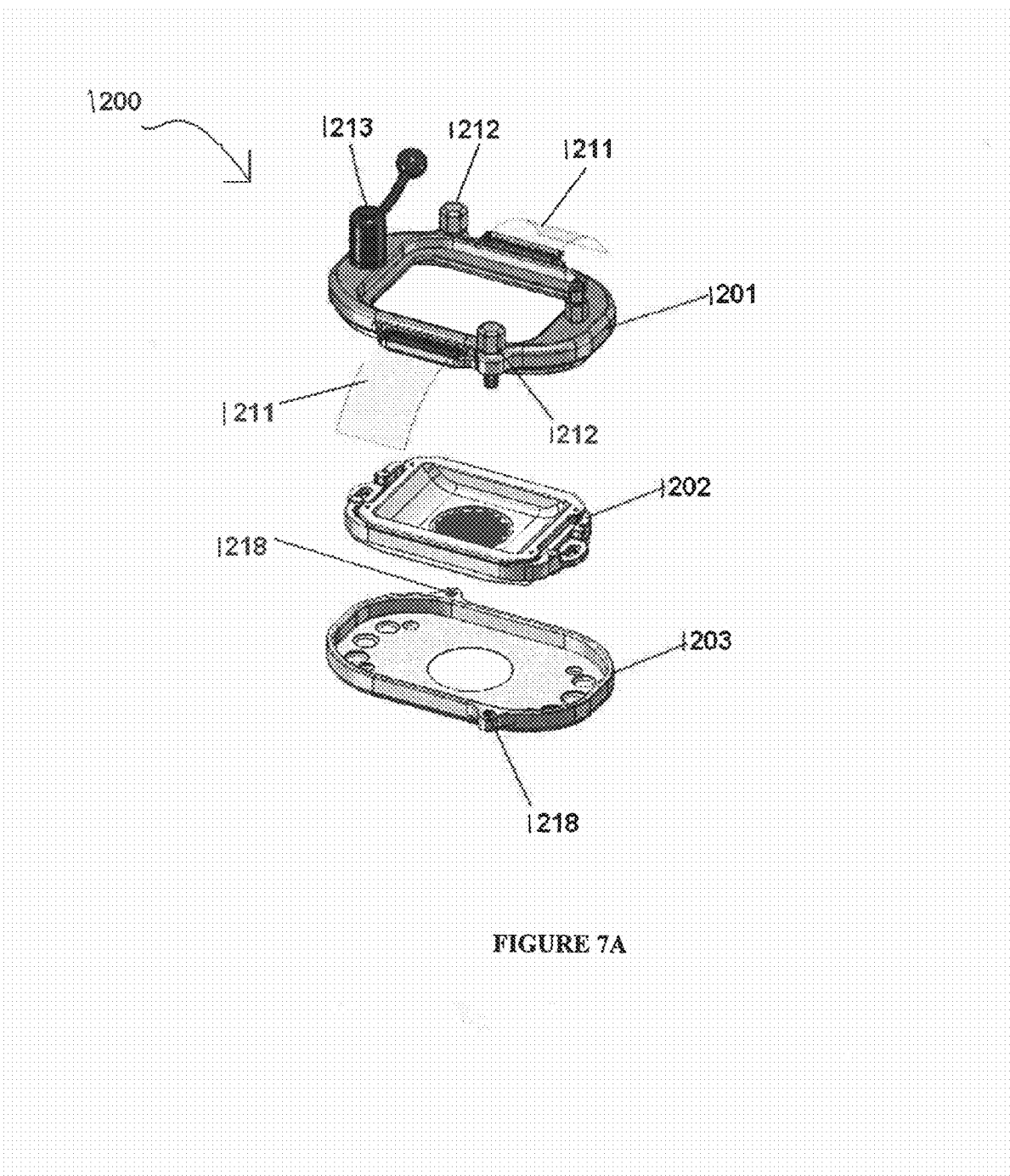
FIG. 7A is a schematic depicting the components of an exemplary embodiment of a blister harvesting device according to the invention.
Figure 7B:
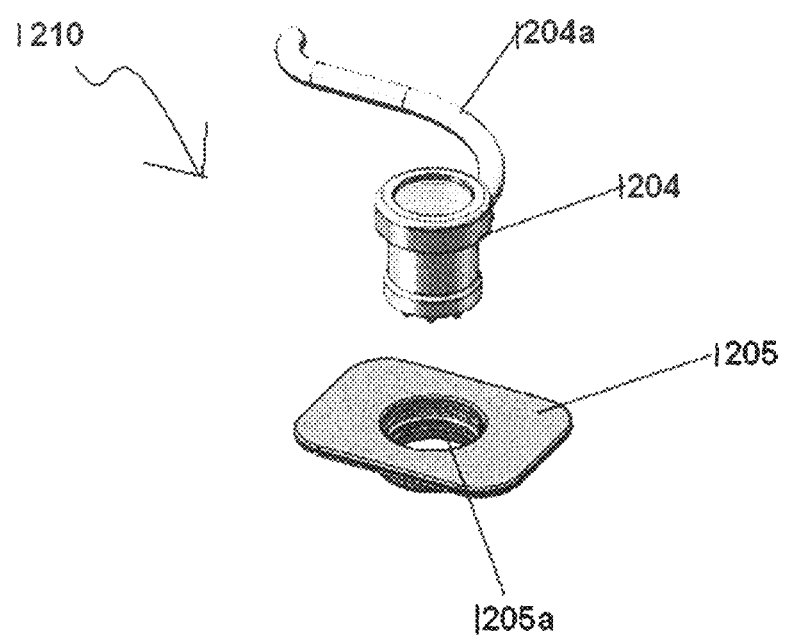
FIG. 7B is a schematic depicting the components of an exemplary embodiment of a blister generation module for coupling with the blister harvesting device of FIG. 7A.
Figure 9:
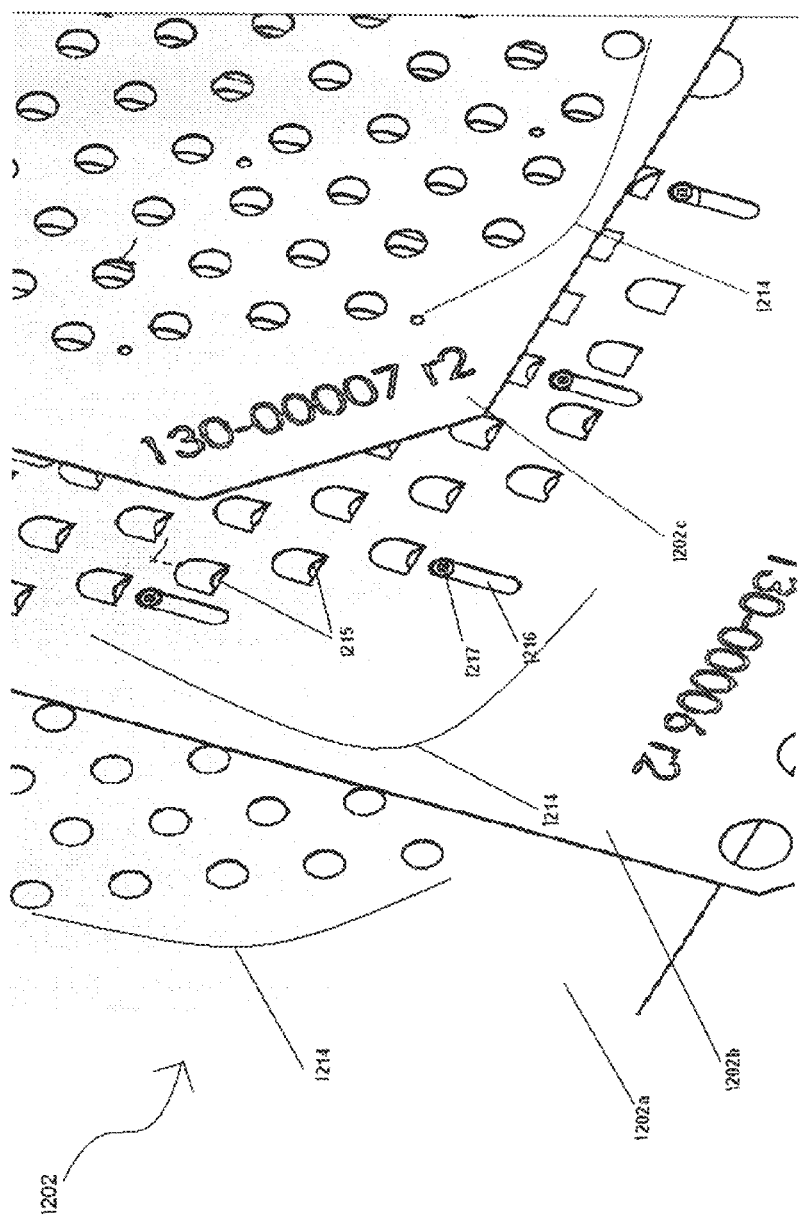
FIG. 9 is a schematic depicting the components of an exemplary embodiment of a cutter assembly for use in the devices according to the invention.
Figure 10A:
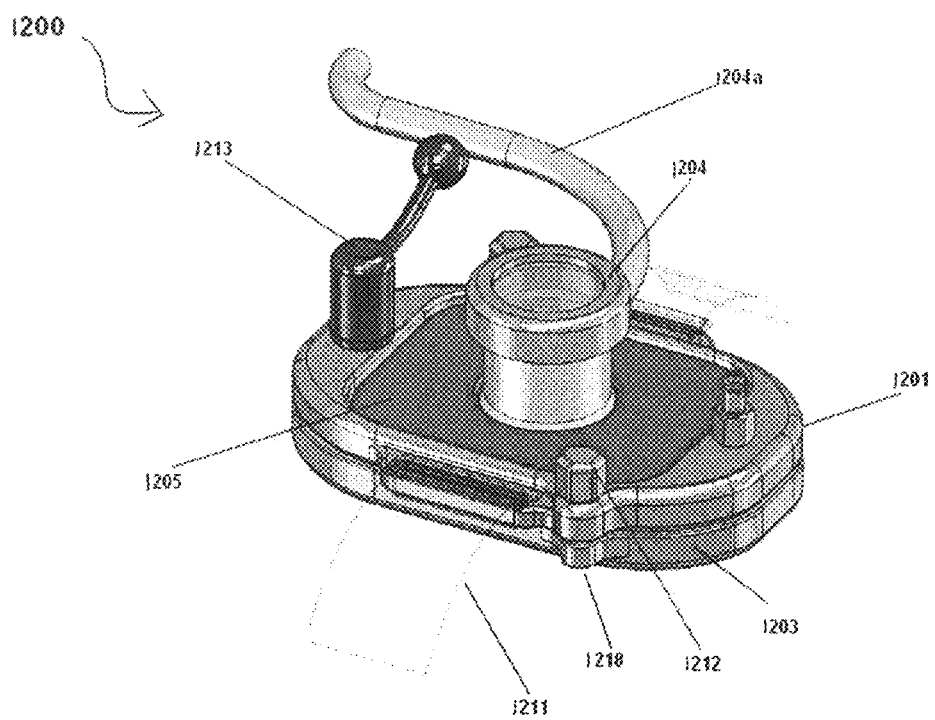
FIG. 10A is a schematic depicting an exemplary embodiment of a device according to the invention in a blister generation mode.
Figure 10B:
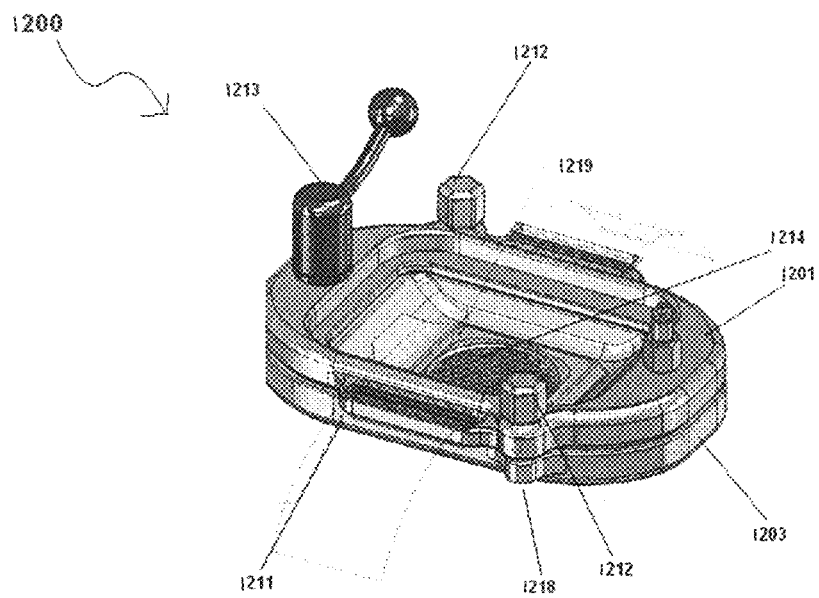
FIG. 10B is a schematic depicting an exemplary embodiment of a device according to the invention in a blister harvesting mode.
Figures 12A, 12B, 12C:
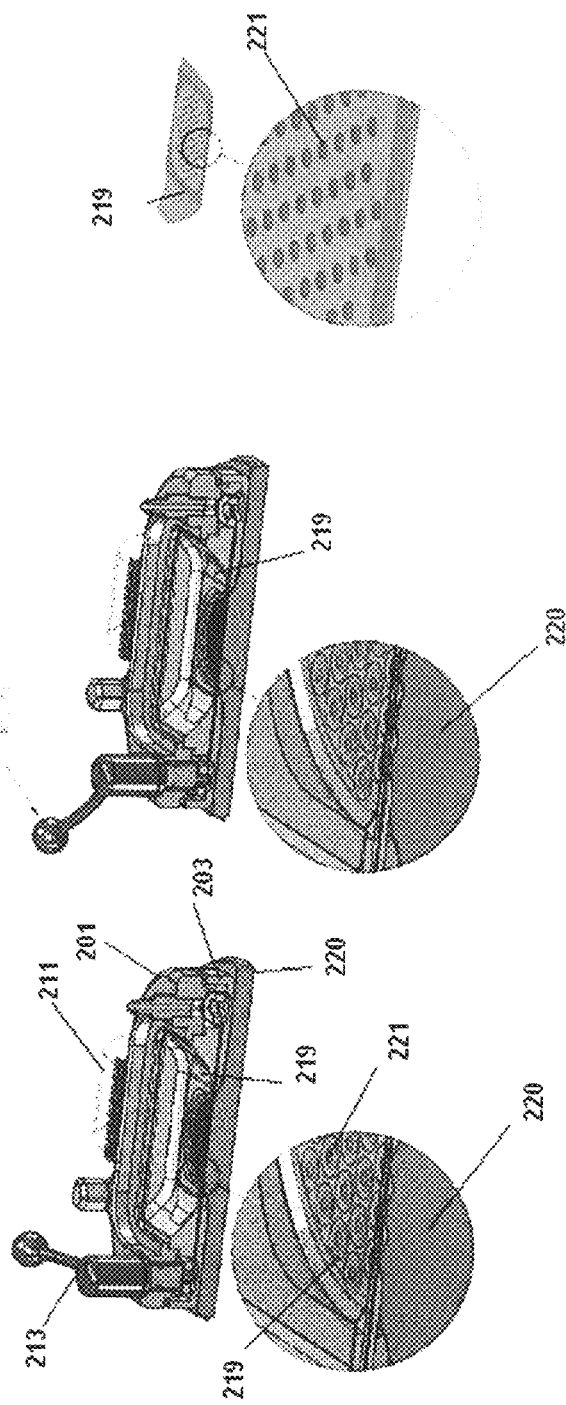
FIG. 12A-12C are schematics depicting the blister harvesting steps using the device mode depicted in FIG. 10B.

Referring now to FIGS. 7A and 7B, device 1200 includes a top housing 1201, a cutter assembly 1202 and a base housing 1203. The top housing includes a rotatable handle 1213 that is coupled to the cutter assembly 1202. The top housing further includes a strap 1211 for coupling the device 1200 (once assembled) against a skin surface. The strap may be adjustable in size, or may be a fixed size. The top housing 1201 is configured to removably receive a blister generation module 1210 that includes a blister generation device 1204 and an adaptor plate 1205 (FIG. 2B).

FIGS. 3A-3C depict the assembly of device 1200. As shown in FIG. 3A, cutter assembly 1202 is inserted into top housing 1201. Top housing 1201 is then coupled to base housing 1203 via one or more threaded screws 1212 that are received by a corresponding threaded holes 1218 in base housing 1203, such that cutter assembly 1202 is disposed in between top housing 1201 and bottom housing 1203 (FIG. 3B). As shown in FIG. 3C, the blister generation module 1210 is then inserted into top housing 1201. In certain embodiments, the bottom of adaptor plate 1205 that interfaces with top housing 1201 includes a gasket around the bottom perimeter of the plate 1205 to create an airtight seal between adaptor plate 1205 and top housing 1201 when coupled together. The blister generation device 1204 of the blister generation module 1210 is coupled to an opening 1205*a* within adaptor plate 1205. In certain embodiments, a gasket is disposed within opening 1205*a* to form an airtight seal between blister generation device 1204 and adaptor plate 1205 when coupled together.

Referring now to FIG. 4, the cutter assembly 1202 of device 1200 is shown. The cutter assembly 1202 includes a bottom plate 1202*a*, a middle plate 1202*b*, and a top plate 1202*c*, each of which include an array of openings 1214 (e.g., holes or slots) (sometimes referred to herein as hole array 1214). One or more openings of the hole array 1214 in the bottom 1202*a*, middle 1202*b* and/or top 1202*c* plates define a cutting edge or surface 1215. Preferably one or more openings in the hole array 1214 of at least the middle plate 1202*b* define a cutting edge or surface 1215 (FIG. 4). The three plates are assembled in a stacked configuration with the middle plate 1202*b* being coupled to the bottom plate 1202*a*, and the top plate 1202*c* being coupled to the middle plate 1202*b*. One or more of plates 1202*a*, 1202*b* and 1202*c* are configured to be movable in a lateral direction relative to each other. For example, the middle plate 1202*b* may be laterally movable relative to the bottom plate 1202*a*, the top plate 1202*c*, or both. The top plate 1202*c* may be movable relative to the middle plate 1202*b*, the bottom plate 1202*a*, or both. In certain embodiments, the one of more of plates 1202*a*, 1202*b* and 1202*c* are configured to laterally move within a fixed distance relative to each other.

The middle plate 1202*b* and/or top plate 1202*c* can be coupled to their respective plates in the stacked configuration via at least one frangible section which serves to keep the plates in alignment until a lateral force is applied to the middle 1202*b* and/or top 1202*c* plate, which breaks the frangible section(s) and allows lateral movement of the plates relative to each other. In a particular embodiment, at least the middle plate 1202*b* is coupled to the bottom plate 1202*a* via at least one frangible section. The at least one frangible section is configured to break when a lateral force is applied to the middle plate 1202*b*, allowing the middle plate 1202*b* to move in a lateral direction relative to the bottom plate 1202*a*, the top plate 1202*c*, or both. Preferably, middle plate 1202*b* is configured to laterally move within a fixed distance relative to the bottom plate 1202*a* and/or top plate 1202*c*. In a particular embodiment, the middle plate 1202*b* includes one or more grooves or channels 1216 that are configured to receive a pin 1217 vertically extending from bottom plate 1202*a*. Pin 1217 is received at one end of channel 1216 when the frangible section is intact, and laterally slides within channel 1216 to the opposite end when the frangible section is broken, such that the lateral movement of plate 1202b relative to plate 1202a and/or 1202c is fixed by the movement of pin 1217 within channel 1216.

One or more coupling members can be disposed between the plates to form the frangible sections, as described in further detail below. The one or more coupling members are disposed between the openings within hole array 1214. Alternatively, the one or more coupling members are disposed between the plates outside of hole array 1214. The frangible coupling of the plate members to each other can be accomplished using a mechanical stamping technique, a mechanical punch technique, spot welding, photo etching, an epoxy, an adhesive, mechanical compression, a snap-fit assembly, a tongue and groove assembly, a post and bar assembly, a frangible pin, or any combination thereof.

In certain embodiments, the middle plate 1202b and/or top plate 1202c can be coupled to their respective plates in the stacked configuration via at least one elastic member or spring member which serves to keep the plates in alignment until a lateral force is applied to the middle 1202b and/or top 1202c plate, which allows the elastic/spring section(s) to flex and allows lateral movement of the plates relative to each other. Upon removal of the lateral force, the elastic/spring sections relax, which allows the plates to return to their original positions such that the hole arrays 1214 between the plates are once again in concentric alignment. The one or more elastic coupling members or spring members can be disposed between the openings within hole array 1214. Alternatively, the one or more elastic coupling members or spring members can be disposed between the plates outside of hole array 1214.

Preferably, the hole arrays 1214 of the bottom 1202a, middle 1202b and top 1202c plates include holes that are substantially similar in size and substantially cylindrical in shape. The size of the holes in each hole array 1214 will depend on the size of the graft needed, with larger holes being used in each plate to produce larger grafts. In certain embodiments, the holes in the hole array 1214 range between 1 mm and 12 mm in diameter, or any specific value in between. For example, the diameter of the holes in the hole array 1214 of one or more of plates 1202a, 1202b and 1202c can be 1 mm, 1.5 mm, 2 mm, 2.5 mm, 3 mm, 3.5 mm, 4 mm, 4.5 mm, 5 mm, 5.5 mm, 6 mm, 6.5 mm, 7 mm, 7.5 mm, 8 mm, 8.5 mm, 9 mm, 9.5 mm, 10 mm, 10.5 mm, 11 mm, 11.5 mm or 12 mm. In certain embodiments, the holes in hole array 1214 vary in size and/or shape between the bottom plate 1202a, middle plate 1202b and/or top plate 1202c. Once plates 1202a, 1202b and 1202c of cutter assembly 1202 are assembled (i.e., in the stacked configuration), the hole array 1214 of each of plates 1202a, 1202b, and 1202c are aligned. In a particular embodiment, hole arrays 1214 of plates 1202a, 1202b, and 1202c are concentrically aligned.

The device 1200 has two modes of operation: 1) a blister generation mode (FIG. 5A); and 2) a blister harvesting mode (FIG. 5B). As shown in FIG. 5A, the blister generation mode includes the assembly with the blister generation module 1210. The blister generation module 1210 is removed from the device assembly for blister harvesting mode (FIG. 5B). To produce and harvest a plurality of substantially planar micrografts, device 1200 in the blister generation mode (i.e., with blister generation module 1210, as shown in FIG. 5A), is placed on a donor site 1220 such as an inner thigh of a patient (FIG. 6A). Strap 1211 is used to keep the device 1200 in place against the skin surface of donor site 1220. The blister generation device 1204 is activated by turning/cranking handle 1204a of blister generation device 1204. The blister generation device 1204 utilizes a vacuum component, a heating component, or a combination thereof, for raising skin blisters. An exemplary heating component is a light source. In a particular embodiment, mechanism is a combination of a vacuum component and a heating component.

In certain embodiments, the blister generation device 1204 is a suction blister device for suction blister grafting. Suction blister grafting involves raising a skin blister, and then cutting off the raised blister. An exemplary suction blister grafting technique is shown in Awad, (Dermatol Surg, 34(9):1186-1193, 2008), the content of which is incorporated by reference herein in its entirety. This article also shows various devices used to form suction blisters. A suction blister device is also described in Kennedy et al. (U.S. Pat. No. 6,071,247), the content of which is incorporated by reference herein in its entirety. An exemplary device is the commercially available Negative Pressure Cutaneous Suction System from Electronic Diversities (Finksburg, Md.).

A device for raising a suction blister typically operates by use of suction chambers that are attached to a patient's skin. An instrument typically contains a power source, a vacuum pump, temperature controls and all related controls to operate multiple suction chambers. The suction chambers are connected to the console by a flexible connection. Each of the chambers is controlled by a preset temperature control to provide an optimal skin warming temperature. Both chambers share an adjustable common vacuum source that affects all chambers equally.

The chamber heating system provides a slight warming of an orifice plate of the device, which is in direct contact with the patient's skin surface. The negative pressure chamber is fabricated of mostly plastic components, with two removable threaded caps. The upper cap is fitted with a clear viewing lens so that the actual blister formation can be observed. The opposite end of the chamber is fitted with a removable orifice plate that is placed on the patient's skin. Since this plate is simply threaded onto the chamber end, multiple plates with different opening patterns can be interchanged as desired.

The interior of the device is warmed and illuminated by an array of low voltage incandescent lamps. This lamp array is controlled from the instrument console temperature controller, cycling as needed, to maintain the set point temperature. The heat from these lamps is radiated and conducted to the orifice plate, which then warms the patient's skin. The chamber is connected to the console via a composite vacuum and low voltage electrical system. Quick connections are used for the vacuum and electrical system to facilitate removal and storage.

The Negative Pressure Instrument console is a self-contained fan cooled unit which is designed to operate on 120 VAC 60 Hz power. Vacuum is supplied by an industrial quality diaphragm type vacuum pump, capable of a typical vacuum of 20 in Hg (0-65 kpa) at 0 CFM. An analog controller that is preset to 40° C. provides the temperature control for each suction chamber. This provides accurate control of the orifice plate temperature. The instrument console has internal adjustments that allow the user to recalibrate the temperature setting if desired. Other temperatures can be preset if desired. The front panel includes a vacuum gauge and vacuum bleeder adjustment to regulate the vacuum to both chambers. The console front panel also contains the connections for the chamber assemblies.

The application of a moderate negative pressure from the blister generation device 1204 causes the patients skin to be gently drawn through the concentrically aligned hole arrays

1214 of plates 1202a, 1202b and 1202c in cutter assembly 1202 (FIG. 6B). Such action results in generation of a plurality of raised microblisters 1221, particularly epidermal microblisters. The blisters 1221 may or may not be fluid-filled. The plurality of suction blisters 1221 generated are of uniform size, approximately the size of the openings/holes in the hole arrays 1214 of the three plates of cutter assembly 1202, and are uniformly spaced in accordance with the configuration of the holes in hole array 1214, such that a plurality of substantially planar microblisters 1221 are generated. The skin and blister area is generally not damaged and patient discomfort is minimal.

Once the substantially planar microblisters 1221 are raised/generated the device is converted into the blister harvesting mode by removing the blister generation module 1210 from the top housing 1201, thereby exposing the hole array 1214 in the top plate 1202c of cutter assembly 1202. At least a portion of the raised microblisters 1221 protrude through the top of the hole array 1214, as shown in FIGS. 6B and 6C. A substrate 1219 is applied to the surface of hole array 1214, as shown in FIGS. 5B and 7A, such that the substrate 1219 is in direct contact with the raised blisters 1221.

To cut the raised blisters 1221, handle 1213 is rotated in a clockwise or counterclockwise direction (FIG. 7B). Handle 1213 is coupled to the middle plate 1202b of cutter assembly 1202 in a configuration that translates the rotational movement of the handle 1213 into lateral movement of middle plate 1202b. The lateral force applied to middle plate 1202b by handle 1213 causes middle plate 1202b to move in a lateral direction relative to bottom plate 1202a and/or top plate 1202c, thereby disrupting the alignment of the hole arrays 1214 between plates 2012a, 2012b and 1202c. The lateral displacement of the hole array 1214 of middle plate 1202b causes the cutting surface 1215 defined by one or more holes in the hole array 1214 to cut the raised blisters 1221. As the raised blisters 1221 are cut, they are simultaneously transferred/retained on substrate 1219 in the same configuration as generated within hole array 1214, resulting in a substrate containing a plurality of micrografts that are uniformly spaced and oriented on the substrate 1219 (i.e., a substrate containing a plurality of substantially planar micrografts).

Certain embodiments of device 1200 integrate consumable/single-use components (e.g., substrate 1219 and/or cutter assembly 1202) and re-usable, sterilizable or cleaned components (e.g., top housing 1201, base housing 1203 and blister generation module 1210), thereby providing a reliable system that is easy to maintain. All components of device 1200 that come into contact with the donor and/or recipient tissue (both single-use and reusable components) must be sterile/sterilized to reduce the risk of infection.

In certain embodiments, substrate 1219 includes an adhesive on one side that facilitates attachment of the blisters to the substrate. The substrate material may have intrinsic adhesive properties, or alternatively, a side of the substrate may be treated with an adhesive material, e.g., an adhesive spray such as LEUKOSPRAY (Beiersdoerf GmbH, Germany). The substrate may be a deformable non-resilient material. A deformable non-resilient material refers to a material that may be manipulated, e.g., stretched or expanded, from a first configuration to a second configuration, and once in the second configuration, there is no residual stress on the substrate. Such materials may be stretched to an expanded configuration without returning to their original size. Such deformable non-resilient materials tend to be soft, stiff or both soft and stiff. Softness is measured on the durometer scale. An example of such a material is a soft polyurethane. A soft polyurethane is produced is as follows. Polyurethanes in general usually have soft and hard segments. The hard segments are due to the presence of phenyl bridges. In a soft polyurethane, the phenyl bridge is switched out for an aliphatic, which is more flexible as its 6 carbon ring has no double bonds. Therefore, all the segments are soft. On the Durometer Scale, a soft polyethylene is rated about Shore 80A. Other materials suitable for use with the device 1200 of the invention include low density polyethylene, linear low density polyethylene, polyester copolymers, polyamide copolymers, and certain silicones. In a particular embodiment, the substrate 1219 is Tegaderm™.

Ultimately, the substrate containing the plurality of uniformly spaced and oriented (i.e., substantially planar) micrografts is applied to a recipient of site of a patient. Prior to applying the grafts to the recipient site, the site is prepared to receive the grafts using any technique known in the art. Necrotic, fibrotic or avascular tissue should be removed. The technique used to prepare the site will depend on damage to the recipient site. For example, epidermal tissue, if present at the recipient site, can be removed to prepare the area for receiving the micrografts. Burned or ulcerated sites may not need removal of epidermal tissue, although some cleaning of the site or other preparation of the site may be performed. Wounds should be debrided and then allowed to granulate for several days prior to applying the graft. Most of the granulation tissue should be removed since it has a tendency to harbor bacteria. Applying silver sulfadiazine to the wound for 10 days prior to grafting reduces the bacterial count greatly.

The size of the area at the recipient site can be about the same size as the area of the substrate having micrografts adhered thereto. This size generally will be greater than the area of the original graft tissue that was removed from the donor site to form the micrografts. The depigmented or damaged skin can be dermabraded with sandpaper or another rough material. Alternatively, the epidermal tissue can be removed from the recipient site by forming one or more blisters over the area to be treated, e.g., a suction blister or a freezing blister, and the raised epidermal blister tissue can then be removed by cutting or another procedure.

The substrate having the substantially planar micrografts can be placed over the area to be treated to form a dressing. A portion of the substrate having the micrografts can be positioned over the area to be repaired, e.g., the area from which the epidermal tissue has been abraded or removed for repigmentation. The substrate can be fixed in place over the treatment area, e.g., using tape or the like. The substrate can be removed after sufficient time has elapsed to allow attachment and growth of the micrografts in the treatment area, e.g., several days to a few weeks.

Manufacturing Uniform Components for Use in Integrated Devices of the Invention

The invention further relates to methods for manufacturing uniform components for use in the integrated devices of the invention.

In order to generate substantially planar micrografts, the components within cutter assembly 1202 must be substantially uniform with respect to one another. In particular, the planar surfaces of the components within cutter assembly 1202 must be substantially uniform.

In certain aspects one or more coupling members are used to create a frangible coupling between at least two of plate members 1202a, 1202b and 1202c. The coupling members are disposed between two or more of the plate members to form a frangible section that is broken upon movement of said plates with respect to each other, as previously described. The tolerance for any inconsistencies between the planar surfaces of the coupling members and one or more of the plate members and/or inconsistent dimensions (e.g., width) between the coupling members and one or more of the plate members is very low and could result in non-planar, non-uniform micrografts and device malfunction.

Inconsistencies between the planar surfaces of different stocks of sheet material, manufacturing methods of blanks for the coupling members and/or plates, and finishing methods of the coupling members and/or plates can each increase tolerance stackups beyond an acceptable level, thereby decreasing the efficiency and function of device and resulting in micrografts that are unusable, and increase patient discomfort/distress.

The accumulated variations in production dimensions of the coupling members, variations in production dimensions of the plate members, and variation in the spacing between plate members, can each increase tolerance stackups and decrease device function. In order to optimize the tolerances within the cutter assembly 1202, the plurality of coupling members are preferably formed from the same sheet stock of material as at least one plate member in the cutter assembly 1202. In a particular embodiment, the plurality of coupling members and at least middle plate member 1202b in cutter assembly 1202 are preferably formed from the same sheet stock of material (e.g., a single sheet stock of material). Forming the coupling members and the middle plate member 1202b from the same sheet stock ensures a uniform thickness between the coupling members and between the coupling members and plate member 1202b, and ensures uniform, planar mating surfaces between the coupling members and plate member 1202b, thereby decreasing tolerance stackups within cutter assembly 1202 and ensuring proper device function.

Plate members 1202a, 1202b, and 1202c can be formed from the same material, or different materials with respect to each other, so long as the materials used result in substantially planar mating surfaces between the three plates. Preferably, plate members 1202a, 1202b, and 1202c are formed from a metallic material (e.g., the same metallic material, or different metallic materials).

In certain embodiments, each of plate member 1202a, 1202b, and 1202c is formed from the same sheet stock of material, preferably a single sheet stock of material. One or more openings (e.g., holes or slots) are formed within each plate member to form hole arrays 1214 that align when the plate members are assembled, as previously described. In certain embodiments, the coupling members are formed from the same sheet stock from which the plurality of plate members are generated. Forming the coupling members and plate members from the same sheet stock ensures uniformity in the thickness among and between the coupling members and plate members, and uniformly planar mating surfaces between the coupling members and plate members, thereby decreasing tolerance stackups within cutter assembly 1202 and ensuring proper device function.

The coupling members can be any shape or dimension sufficient to couple the plates together without obstructing the holes in the hole arrays 1214 through which the suction blisters are raised. For example, the coupling members can be substantially square or rectangular in shape. Alternatively, the coupling members are substantially circular in shape. In certain embodiments, the coupling members are of a sufficient shape and size for location between the holes of the hole arrays 1214 of the plate members. In other embodiments, the coupling members are of a sufficient shape and size for location along the edges of the plurality of plates.

Any method can be used to manufacture the plates and/or coupling members, such as drilling, milling, laser etching, lithographic processing, photo etching, laser ablation and the like. In a particular embodiment, a photo etching process is used to manufacture the plates and/or coupling members.

The frangible coupling between the coupling members and plate members can be accomplished using a variety of techniques. For example, the coupling members can be frangibly coupled between the plate members via spot welding techniques (e.g., laser spot welding), via an adhesive such as epoxy, polyurethane, acrylic or a resin, via a frangible pin, a snap-fit or tongue and groove assembly. Such frangible coupling techniques can be accomplished using one or more manufacturing processes such as cold-heading, multiple-die forming, multiple-die progression, multiple-die headers, casting, stamping, punching, atomic hydrogen welding, bare metal arc welding, carbon arc welding, flux cored arc welding, gas metal arc welding, gas tungsten arc welding, plasma arc welding, shielded metal arc welding, submerged arc welding, air acetylene welding, oxyacetylene welding, oxygen/propane welding, oxy hydrogen welding, pressure gas welding, resistance spot welding, resistance seam welding, projection welding, flash welding, upset welding, co-extrusion welding, cold pressure welding, diffusion welding, explosion welding, electromagnetic pulse welding, forge welding, friction welding, friction stir welding, hot pressure welding, hot isostatic pressure welding, roll welding, ultrasonic welding, electron beam welding, electroslag welding, flow welding, induction welding, laser beam welding, percussion welding, thermite welding, electrogas welding, and stud arc welding.

Optionally, a portion of the plate material at or around the site of the frangible coupling is removed to accommodate at least a portion of the coupling member by forming a depression at or around the frangible section. For example, in one embodiment, laser etching or photo etching on the plate member is used to circumscribe the coupling point at or proximal to the frangible coupling. In another embodiment, a depression at or proximal to the plate member can be removed with any method known in the art, for example drilling, milling, laser etching, photo etching, laser ablation and the like.

Figure 13:
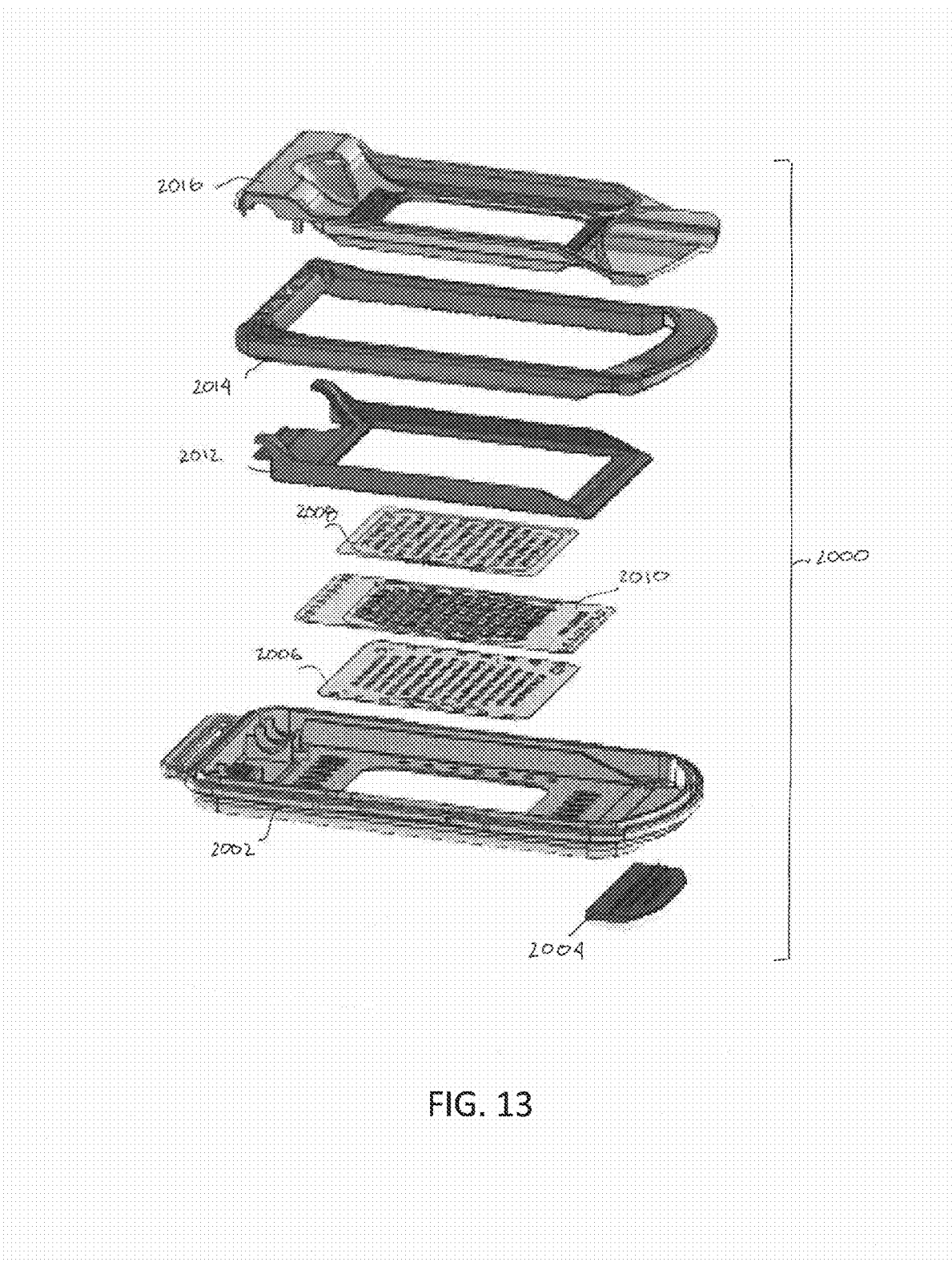
FIG. 13 is exploded schematic perspective view of another embodiment of a skin harvester according to the invention.

FIG. 13 is exploded view of another embodiment of a skin harvester according to the invention. Harvester 2000 includes a bottom element 2002 with a strap coupler 2004 (e.g., for joining a hook and fastener-type strap to the harvester to facilitate attachment of the harvester 2000 to a patient's skin, e.g., by wrapping the device around a patient's leg for harvesting skin from the inner thigh).

The harvester 2000 also includes a cutter assembly with a bottom plate 2006, a top plate 2008 and a middle (cutter) plate 2010 configurable to initially provide concentrically aligned holes through which blisters can be raised. (The operation of the plates, 2006, 2008 and 2010 of the cutter assembly is similar to that of elements 1202a, 1202b and 1202c described above in connection with FIGS. 7-12.) The harvester 2000 further includes a cutter drive sled 2012, handle actuator 2014 and a top element 2016.

Figure 13A:
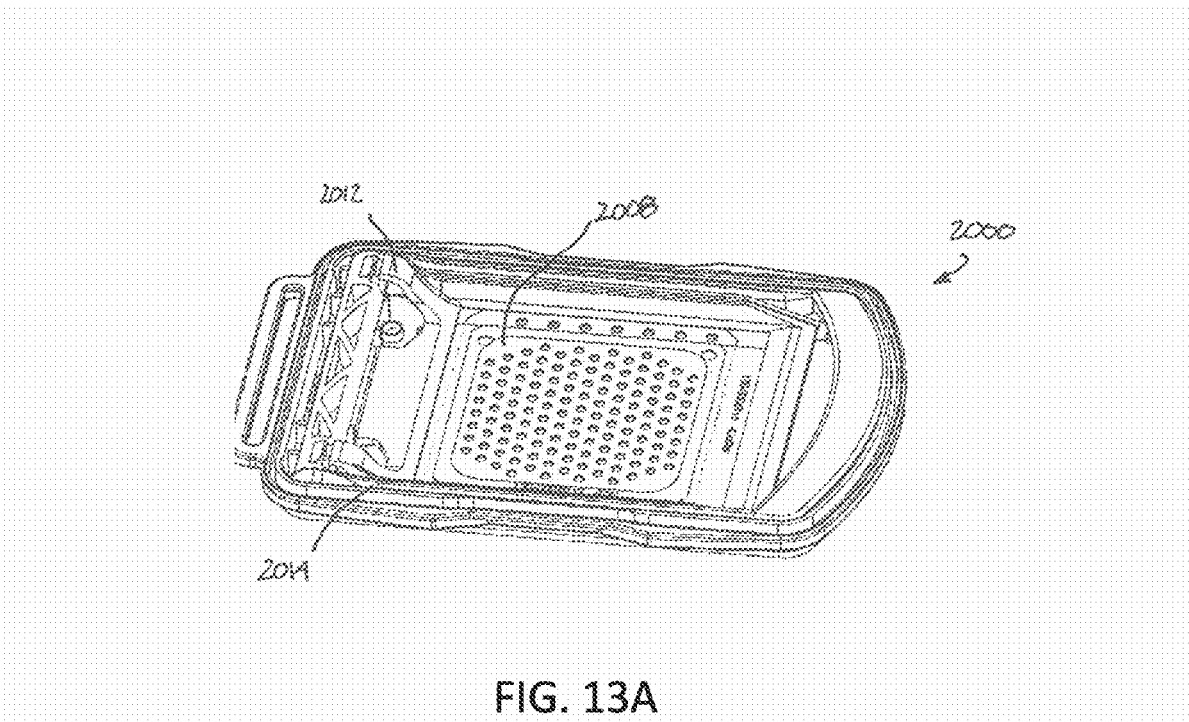
FIG. 13A is a schematic perspective view of the harvester of FIG. 13 as assembled.
Figure 13B:
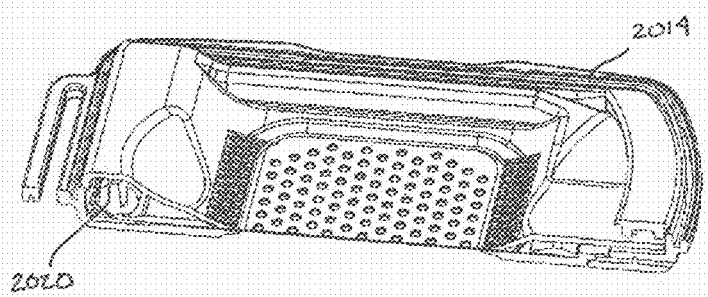
FIG. 13B is a schematic perspective sectional view of the harvester of FIG. 13.

FIG. 13A is a schematic perspective view of the harvester 2000 as assembled (with top element 2016 omitted for clarity). FIG. 13B is a schematic perspective sectional view of the harvester 2000.

Figure 13C:
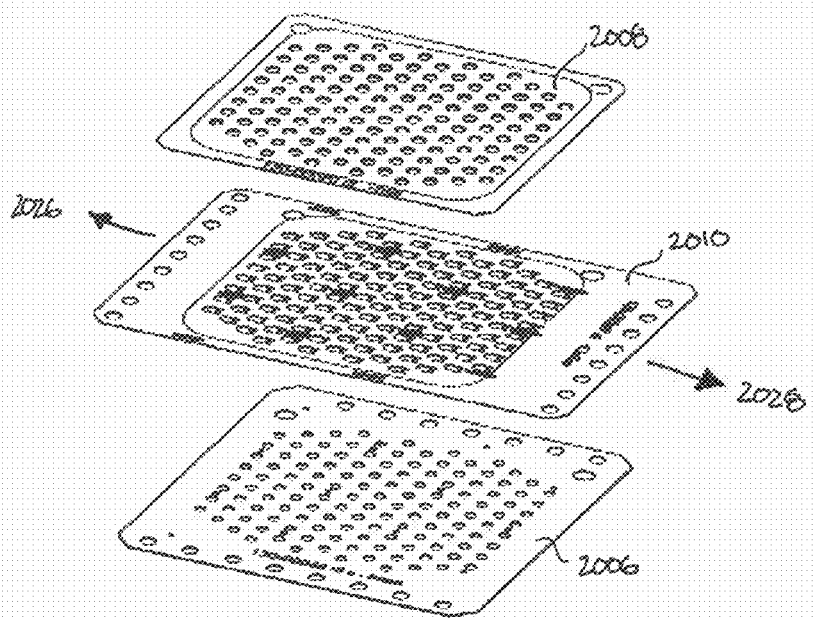
FIG. 13C is an exploded schematic perspective view of the cutter and guide plates of the harvester of FIG. 13.
Figure 13D:
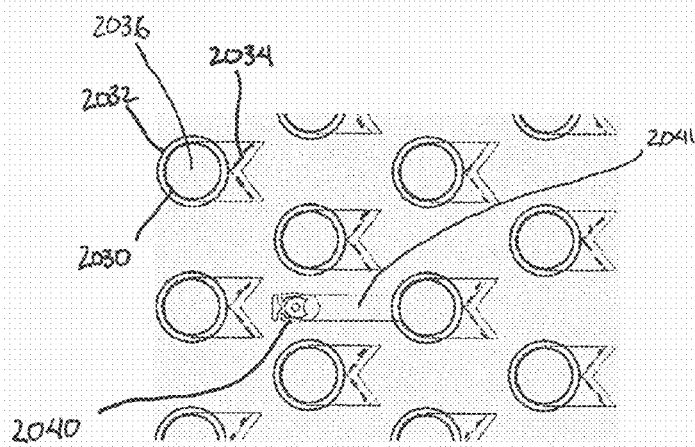
FIG. 13D is a top view of the cutter and guide plates of the harvester of FIG. 13.

FIG. 13C is an exploded schematic perspective view of the guide and cutter plates 2006, 2008 and 2010 of the harvester 2000. As described above in FIGS. 7-12, the cutter plate 2010 is designed to move a direction parallel to guide plates 2006 and 2008 in a one-time, back and forth motion. Following the formation of microblisters that protrude through the aligned holes, the cutter plate moves in the direction 2026 to slice the blisters and then moved in the opposite direction 2028 to at least partially retract the blade elements. The alignment of the plates is further illustrated in FIG. 13D, which is a top view of the cutter and guide plates in a configuration where the top holes 2032, bottom holes 2030 and cutter plate holes 2036 are aligned to permit blisters to form and pass through all three plates (The holes of the top plate can be larger than those of the bottom plate to facilitate blister formation and/or growth of the blister.) The cutter plate holes, however, also provide a cutting edge 2034 (shown in phantom) to occlude the passageway and cleave the blister when the plate 2010 is moved relative to the top and bottom guide plates 2006, 2008. FIG. 13D further illustrate one of a plurality of plate connecting posts 2040 that join the top and bottom plates together and an alignment slot 2041 which allows the cutter plate to move relative to the stationary top and bottom plates 2006, 2008.

The various features of the cutting plate can be formed, for example, lithographically by depositing a resist and patterning it (e.g., by expose to light) such that portions of an initial plate blank are protected from etching while other portion can be removed by etching (e.g., to form the holes and alignment slots). The resist can also be patterned to provide a limited amount of protection to the cutting edge portions, thereby shaping them to have less thickness (e.g., like a knife edge). The sharpness of the cutting edges can be further enhanced by electro-polishing which will reduce the overall thickness of the cutting plate.

Figure 13E:
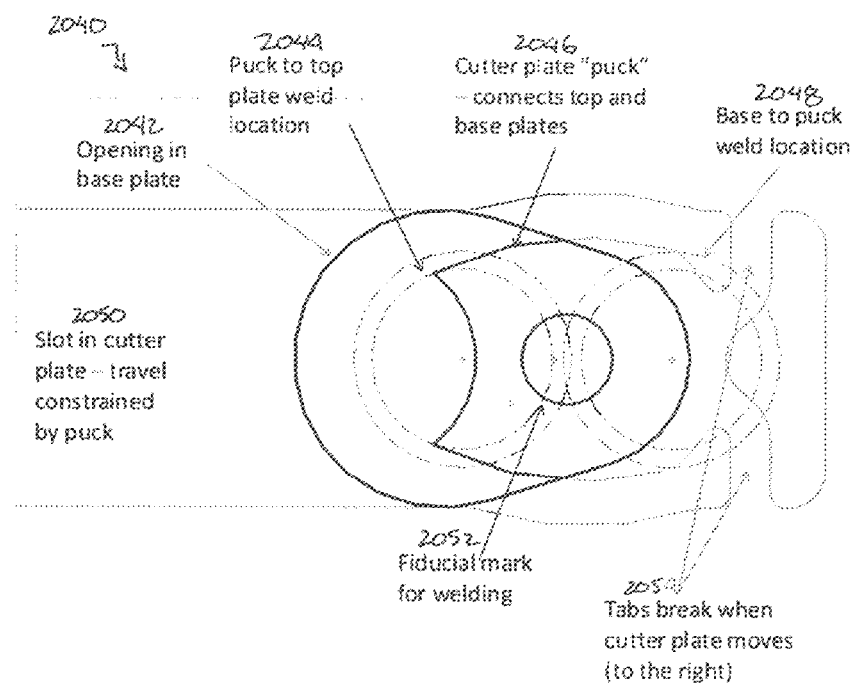
FIG. 13E is a top view of a plate connector assembly of the harvester of FIG. 13.

FIG. 13E (taken in conjunction with FIGS. 13C and 13D) illustrate one way to provide a plate connector assembly. The vertical posts 2040 can be formed by spot welding the top, bottom and cutter plates together. However, the portion of the cutter plate ("puck" 2046) that joins the top and bottom plates in the weld is designed to break away from the cutter plate 2010, e.g., at the initiation of the cutting stroke.

Figure 14A:
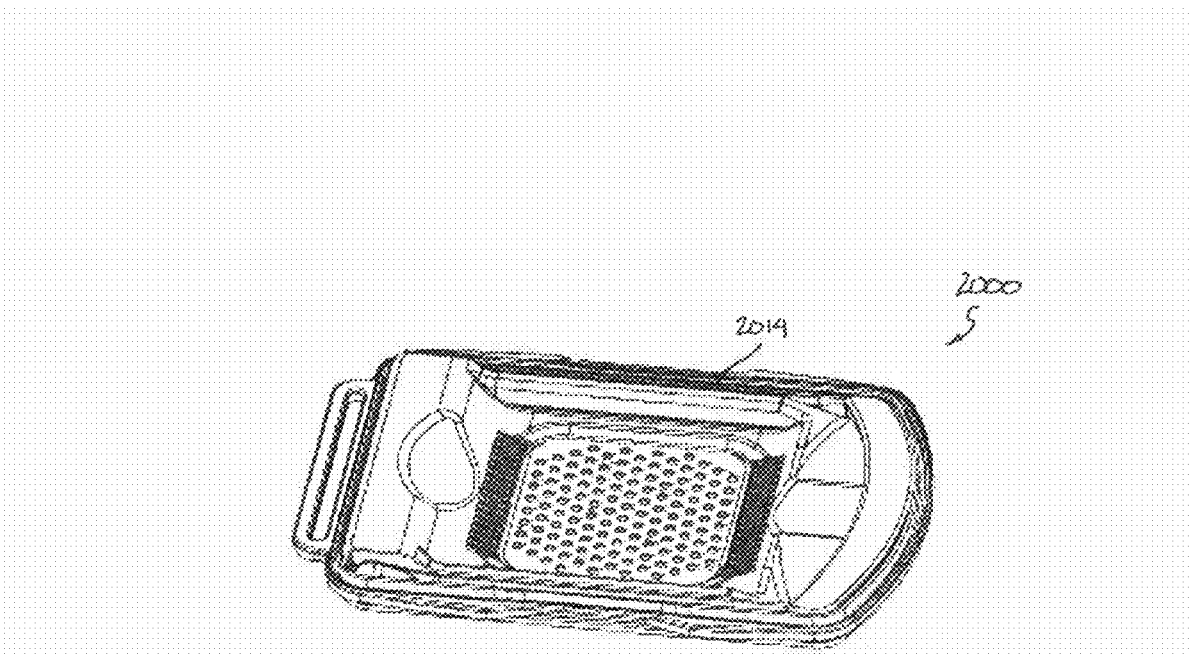
FIG. 14A is a perspective view of the harvester of FIG. 13 in an initial position to further illustrate the cutting mechanism.
Figure 14B:
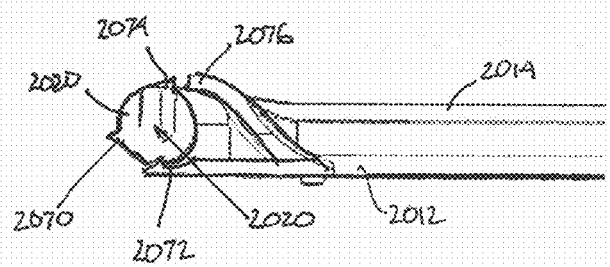
FIG. 14B is sectional side view of the cutter plate drive elements of the harvester in an initial position.

The actuator for moving the cutter plate will now be described in connection with FIGS. 14-18. FIG. 14A is a perspective view of the harvester of FIG. 13 in an initial position with the handle (actuator) 2014 in an initial position. The cutter plate 2010 is joined to a sled 2012 as discussed above. The handle is linked to the sled 2012 via a generally cylindrical bar (axle) 2020. As shown in FIG. 14B the cylindrical bar 2020 rotates about an axis when the handle is lifted up or closed. Cylindrical bar 2020, however also has two non-symmetric features: protrusions 2070 and 2074. The handle 2014 thus serves as a lever arm.

Figure 15A:
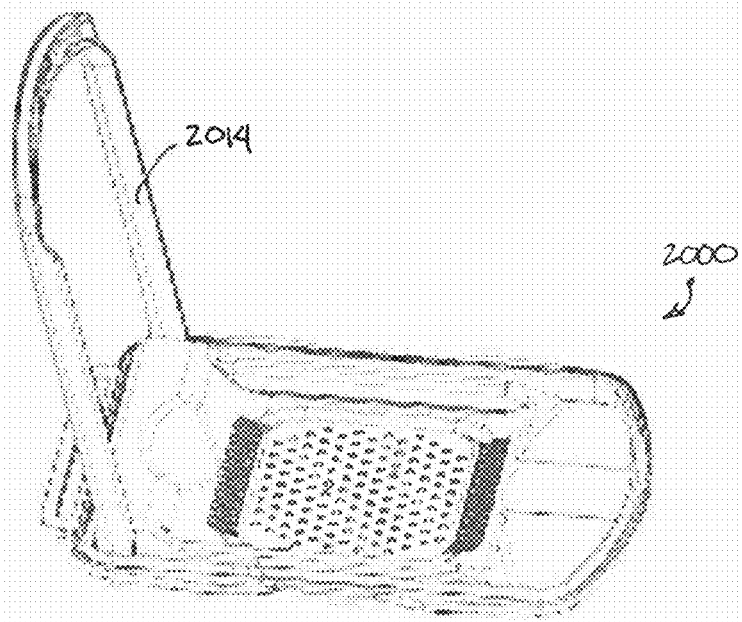
FIG. 15A is a perspective view of the harvester of FIG. 13 in a cocked position (handle up) to further illustrate the cutting mechanism.
Figure 15B:
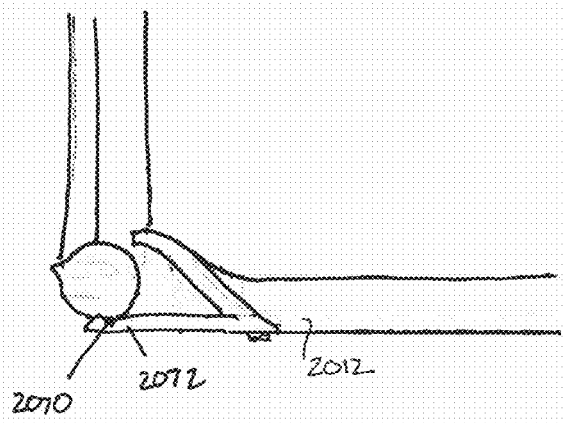
FIG. 15B is sectional side view of the cutter plate drive elements of the harvester in the cocked position.
Figure 16A:
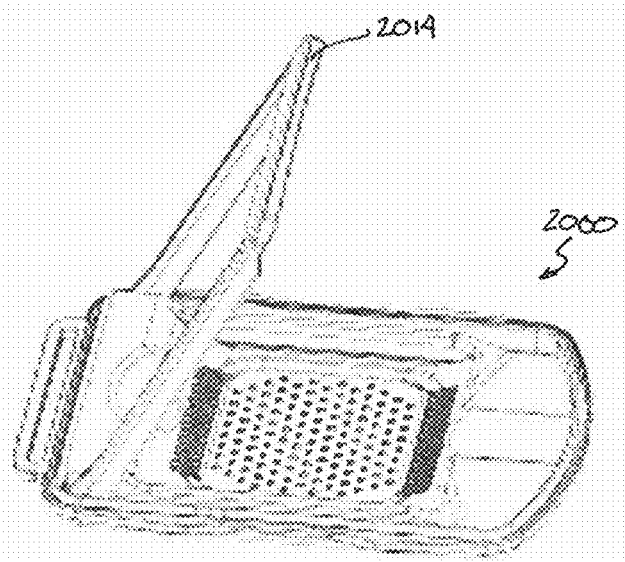
FIG. 16A is a perspective view of the harvester of FIG. 13 in a mid-cut position to further illustrate the cutting mechanism.
Figure 16B:
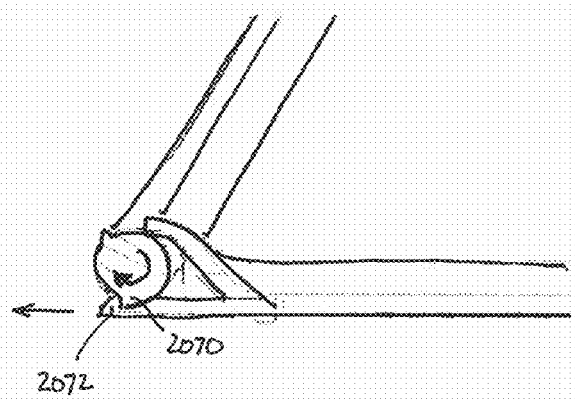
FIG. 16B is sectional side view of the cutter plate drive elements of the harvester in mid-cut position.
Figure 17A:
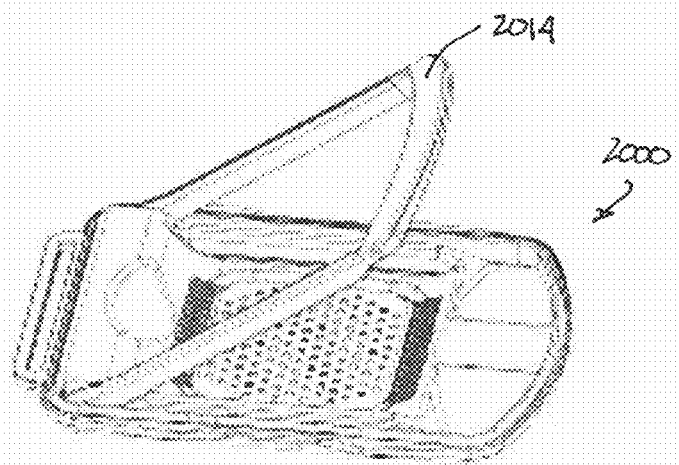
FIG. 17A is a perspective view of the harvester of FIG. 13 in transitional position (from cutting to retraction) to further illustrate the cutting mechanism.
Figure 17B:
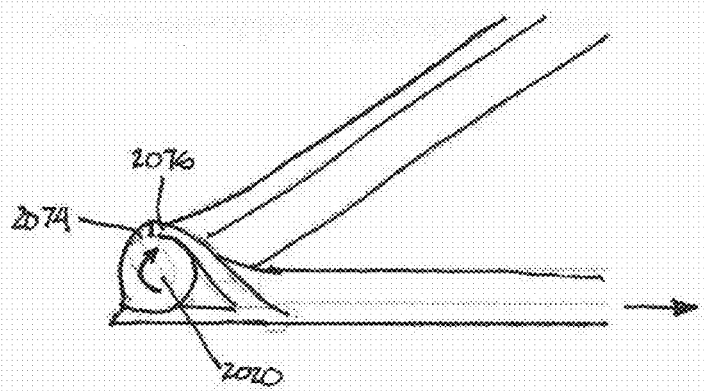
FIG. 17B is sectional side view of the cutter plate drive elements of the harvester in the cut-to-retract transitional position.
Figure 18A:
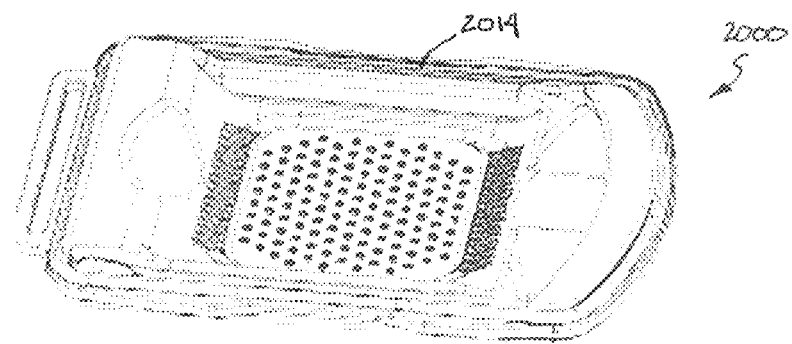
FIG. 18A is a perspective view of the harvester of FIG. 13 in a final (stroke completion) position to further illustrate the cutting mechanism.
Figure 18B:
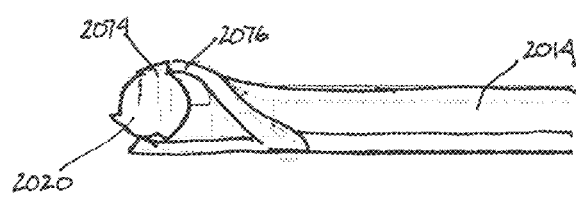
FIG. 18B is sectional side view of the cutter plate drive elements of the harvester in the final (partially retracted) position.

FIG. 15A is a perspective view of the harvester in a cocked position (handle up) to further illustrate the cutting mechanism. As shown in FIG. 15B this results in protrusion 2070 (e.g., a longitudinal ridge on the cylindrical axle) engaging with a mating feature 2072 (e.g., a groove in the sled). As the handle is brought down the sled is thus forces to move by the rotation of axle 2020. FIGS. 16A and 16B illustrates the handle in a in a mid-cut position FIG. 17A is a perspective view of the harvester of FIG. 13 in transitional position (from cutting to retraction) to further illustrate the cutting mechanism. At this point in the rotation of the axle 2020, protrusion 2070 has detached from mating feature 2072 and the second protrusion 2074 has engaged with a different portion 2076 (e.g., a shoulder pad) of the sled. As the handle continues its downward portion, the rotation of axle causes the sled to move in the opposition direct and, thus retract the cutter plate. FIGS. 18A and 18B illustrate the harvester in a final (stroke completion) position.

Figure 1:
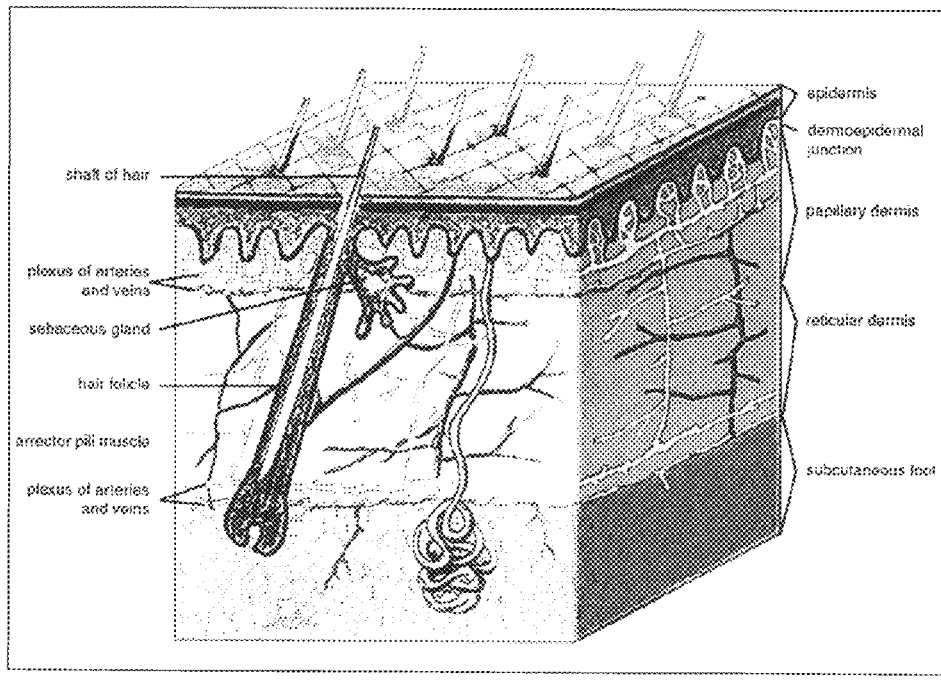
FIG. 1 provides a diagram showing the anatomy of skin.

In certain embodiments, devices of the invention are configured to produce epidermal grafts. The skin consists of 2 layers. The outer layer, or epidermis, is derived from ectoderm, and the thicker inner layer, or dermis, is derived from mesoderm. The epidermis constitutes about 5% of the skin, and the remaining 95% is dermis. FIG. 1 provides a diagram showing the anatomy of skin. The skin varies in thickness depending on anatomic location, gender, and age of the individual. The epidermis, the more external of the two layers, is a stratified squamous epithelium consisting primarily of melanocytes and keratinocytes in progressive stages of differentiation from deeper to more superficial layers. The epidermis has no blood vessels; thus, it must receive nutrients by diffusion from the underlying dermis through the basement membrane, which separates the 2 layers.

The dermis is a more complex structure. It is composed of 2 layers, the more superficial papillary dermis and the deeper reticular dermis. The papillary dermis is thinner, including loose connective tissue that contains capillaries, elastic fibers, reticular fibers, and some collagen. The reticular dermis includes a thicker layer of dense connective tissue containing larger blood vessels, closely interlaced elastic fibers, and coarse, branching collagen fibers arranged in layers parallel to the surface. The reticular layer also contains fibroblasts, mast cells, nerve endings, lymphatics, and some epidermal appendages. Surrounding the components of the dermis is the gel-like ground substance composed of mucopolysaccharides (primarily hyaluronic acid), chondroitin sulfates, and glycoproteins.

In a graft, the characteristics of the donor site are more likely to be maintained after grafting to a recipient site as a function of the thickness of the dermal component of the graft. However, thicker grafts require more favorable conditions for survival due to the requirement for increased revascularization. It has been discovered, however, that a substantially epidermal graft according to the invention is more likely to adapt to the characteristics of the recipient site.

An epidermal graft refers to a graft that consists of substantially epidermal skin and does not include any substantial portion of the dermal layer. A split thickness graft refers to a graft that includes sheets of superficial (epithelial) and some deep layers (dermal) of skin. A full-thickness graft refers to a graft that includes all of the layers of the skin including blood vessels.

Devices of the invention may be used to harvest a skin graft(s) for repair of numerous different types of skin damage. For example, harvested grafts may be used to treat burns (e.g., both thermal and chemical burns), blistering, dermatological conditions (e.g., epidermolysis bullosa or pyoderma gangrenosum), radiation therapy ulcers, diabetic ulcers, ischemic ulcers, trophic ulcers, trauma, or depigmentation (e.g., vitiligo).

In particular embodiments, the skin graft(s) are used to treat vitiligo. Vitiligo is a chronic disorder that causes depigmentation of patches of skin. It occurs when melanocytes, the cells responsible for skin pigmentation, die or are unable to function. Although patches are initially small, they often enlarge and change shape. When skin lesions occur, they are most prominent on the face, hands and wrists. Some lesions have hyper-pigmentation around the edges. Depigmentation is particularly noticeable around body orifices, such as the mouth, eyes, nostrils, genitalia and umbilicus.

Vitiligo is generally classified into two categories, non-segmental vitiligo and Segmental vitiligo. In non-segmental vitiligo (NSV), there is usually some form of symmetry in the location of the patches of depigmentation. New patches also appear over time and can be generalized over large portions of the body or localized to a particular area. Vitiligo where little pigmented skin remains is referred to as vitiligo universalis. Non-segmental vitiligo can come about at any age, unlike segmental vitiligo which is far more prevalent in teenage years.

Segmental vitiligo (SV) differs in appearance, aetiology and prevalence from associated illnesses. Its treatment is different from that of non-segmental vitiligo. It tends to affect areas of skin that are associated with dorsal roots from the spine. It spreads much more rapidly than non-segmental vitiligo and, without treatment, it is much more stable/static in course and not associated with auto-immune diseases.

To treat vitiligo, an autograft is provided to the site of depigmented skin. The graft includes melanocytes, and thus upon the recipient site accepting the graft, the graft will produce pigmented skin at the recipient site. A donor site of pigmented skin is aseptically cleaned prior to harvesting of a skin graft. Standard methods are used to clean the donor site. A typical donor site is an inner thigh, but any area of pigmented skin may be used.

After cleaning, a skin grafted is harvested using devices of the invention. Devices described herein raise and cut a blister(s), such as a suction blister. The area of depigmented skin (i.e., the recipient site), is prepared through aseptic cleaning and dermabrasion. The graft(s) is applied to the dermabraded recipient site. The donor site and the recipient site are dressed and wound care is provided.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein.

What is claimed:

1. A device for obtaining a skin graft, the device comprising:
    a head adapted for coupling to a cutting body that is disposable on a patient's skin and further adapted for coupling to a vacuum source,
    the head comprising
        a sealing surface to engage with a mating surface on the cutting body such that, when the head is engaged with the cutting body on a patient's skin, an evacuated chamber is formed over a target region of skin;
        a heating element for raising the temperature of the target region of skin; and
        at least one viewing window integrated within the head for concurrently observing a plurality of blisters formed by heating the skin in the evacuated chamber;
    the cutting body comprising
        a cutter plate; and
        an actuator for moving the cutter plate from a first position to a second position and at least partially retracting the cutter plate from said second position.

2. The device of claim 1, wherein the at least one window is formed on a side surface of the head so as to provide a non-parallel viewing angle to the patient's skin.

3. The device of claim 1 wherein the head further comprises at least one light source for illuminating skin blisters as they are being raised.

4. The device of claim 3 wherein the light source is a light emitting diode (LED).

5. The device of claim 1, wherein said viewing window comprises a substantially transparent material.

6. The device of claim 5, wherein said substantially transparent material is selected from the group consisting of an optical polymer, an optical glass, and an optical crystal.

7. The device according to claim 1, wherein at least a portion of said viewing window further comprises a magnification lens.

8. The device according to claim 7, wherein said magnification lens magnifies objects at a magnification ranging from about 2× to about 100×.

9. The device according to claim 1, wherein said viewing window comprises one or more materials selected from an anti-fogging material, an anti-scratch coating, and an anti-glare coating.

10. The device according to claim 1, wherein said viewing window comprises a heat resistant material.

11. The device according to claim 1, wherein at least a portion of said viewing window comprises an ocular shield configured for attenuating entrance of ambient light.

12. The device according to claim 1, wherein the head further comprising at least one temperature measuring element for measuring the temperature of the skin or evacuated chamber.

13. The device according to claim 12, wherein the at least one temperature measuring element comprises at least one thermistor.

14. The device according to claim 1 wherein the heating element is a resistive electrical heating element.

15. The device of claim 1, wherein said cutter plate is coupled to a sled.

16. The device of claim 15, wherein said actuator comprises a handle and a cylindrical bar linking the handle to the sled, said cylindrical bar having a first and a second non-symmetric protrusion, wherein said first protrusion engages with a mating groove in the sled when the handle is in a cocked position such that as the handle is rotated, the sled is forced to move by rotation of the cylindrical bar, thereby moving the cutter plate from said first position to said second position.

17. The device of claim 16, wherein said actuator is configured such that at a transitional state during rotation of the handle the first protrusion detaches from said groove and the second protrusion engages with another position of the sled so as to cause the sled to move in the opposite direction, thereby retracting the cutter plate from said second position.

* * * * *